(12) United States Patent
Shay et al.

(10) Patent No.: US 6,294,650 B1
(45) Date of Patent: *Sep. 25, 2001

(54) INHIBITION OF MAMMALIAN TELOMERASE BY PEPTIDE NUCLEIC ACIDS

(75) Inventors: Jerry W. Shay, Dallas; Woodring E. Wright, Arlington, both of TX (US); Mieczyslaw A. Piatyszek, Morgan Hill, CA (US); David R. Corey; James C. Norton, both of Dallas, TX (US)

(73) Assignee: The Board of Regents, University of Texas System, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/349,532

(22) Filed: Jul. 8, 1999

Related U.S. Application Data

(63) Continuation of application No. 08/838,545, filed on Apr. 9, 1997, now Pat. No. 6,046,307, which is a continuation-in-part of application No. 08/630,019, filed on Apr. 9, 1996, now Pat. No. 6,015,710.

(51) Int. Cl.$^7$ ............................ C07K 7/00; C07K 14/00; C07H 21/00
(52) U.S. Cl. ................... 530/329; 530/324; 530/325; 530/326; 530/327; 530/328; 530/350; 536/24.5
(58) Field of Search .......................... 435/6, 7.1, 7.21, 435/325, 375; 530/300, 324, 325, 326, 327, 328, 329, 350; 514/12, 13, 14, 15, 16, 17, 44; 536/22.1, 23.1, 24.3, 24.31, 24.5; 424/450

(56) References Cited

U.S. PATENT DOCUMENTS

| | | |
|---|---|---|
| 5,583,016 | 12/1996 | Villeponteau et al. ............. 435/91.3 |
| 6,015,710 * | 1/2000 | Shay et al. ........................... 435/375 |
| 6,046,307 * | 4/2000 | Shay et al. ........................... 530/324 |

FOREIGN PATENT DOCUMENTS

| | | |
|---|---|---|
| WO 96/01614 | 1/1996 | (WO) . |
| WO 96/01835 | 1/1996 | (WO) . |
| WO 14026 | 4/1997 | (WO) . |

OTHER PUBLICATIONS

Antisense '97: A roundtable on the state of the industry. Nature Biotechnol. 15 (1997), 519–524.*

Gewirtz, et al. Facilitating oligonucleotide delivery: Helping antisense deliver on its promise. Proc. natl. Acad. Sci. USA 93 (1996), 3161–3163.*

Gura, T. Antisense has growing pains. Science 270 (1995), 575–577.*

Rojanasakul, Y. Antisense oligonucleotide therapeutics: Drug delivery and targeting. Adv. Drug Delivery Rev. 18 (1996), 115–131.*

Stull et al. Antigene, ribozyme and aptamer nucleic acid drugs: Progress and prospects. Pharm. Res. 12 (1995), 465–483.*

Wittung et al. Phospholipid membrane permeability of peptide nucleic acid. FEBS Letts. 365 (1995), 27–29.*

Corey, David R. "Peptide nucleic acids: expanding the scope of nucleic acid recognition", *Trends Biotechnol.*, 15:224–229 (1997).

Derossi, Daniele, et al. "The Third Helix of the Antennapedia Homeodomain Translocates through Biological Membranes", *The Journal of Biological Chemistry*, 269(14):10444–10450 (1994).

Fåhraeus, Robin, et al. Inhibition of pRb phosphorylation and cell–cycle progression by a 20–residue peptide derived from p16CDKN2/INK4A, *Current Biology*, 6(1):84–91 (1996).

Holt, Shawn E., et al. "Refining the telomere–telomerase hypothesis of aging and cancer", *Nature Biotechnology*, 14:836–839 (1996).

Lin, Yao–Zhong, et al. "Inhibition of Nuclear Translocation of Transcription Factor NF—κB by a Synthetic Peptide Containing a Cell Membrane–permeable Motif and Nuclear Localization Sequence", *The Journal of Biological Chemistry*, 270(4):14255–14258 (1995).

Prochiantz, Alain "Getting hydrophilic compounds into cells: lessons from homeopeptides", *Current Opinion in Neurobiology*, 6:629–634 (1996).

Avilion, Ariel A., et al. "Human Telomerase RNA and Telomerase Activity in Immortal Cell Lines and Tumor Tissues", *Cancer Research*, 56:645–650 (1996).

Albanell, Juan, et al. "Telomerase Activity is Repressed during Differentiation of Maturation–sensitive but not Resistant Human Tumor Cell Lines", *Cancer Research*, 56:1503–1508 (1996).

Bodnar, Andrea G., et al. "Mechanism of Telomerase Induction during T Cell Activation", *Experimental Cell Research*, 228:58–64 (1996).

Soder, Anja I., et al. "Amplification, increased dosage and in situ expression of the telomerase RNA gene in human cancer", *Oncogene*, 14:1013–1021 (1997).

Hamilton, Susan E., et al. "Telomerase: anti–cancer target of just a fascnating enzyme?", *Chemistry & Biology*, 3:863–867 (1996).

Yashima, K., et al. "Telomerase activity and in situ telomerase RNA expression in malignant and non–malignant lymph nodes", *J. Clin. Pathol.*, 50:1–7 (1997).

(List continued on next page.)

Primary Examiner—Robert A. Schwartzman
Assistant Examiner—Thomas G. Larson
(74) Attorney, Agent, or Firm—Townsend and Townsend and Crew LLP

(57) ABSTRACT

The invention relates to peptide nucleic acids that inhibit telomerase activity in mammalian cells.

13 Claims, 7 Drawing Sheets

OTHER PUBLICATIONS

Greider, Carol W., et al. "A telomeric sequence in the RNA of *Tetrahymena* telomerase required for telomere repeat synthesis", *Nature*, 337:331–337 (1989).

Melek, Meni, et al. "Oligonucleotides Complementary to the *Oxytricha nova* Telomerase RNA Delineate the Template Domain and Uncover a Novel Mode of Primer Utilization", *Molecular and Cellular Biology*, 14(12):7827–7838 (1994).

Lansdorp, Peter M., et al. "Heterogeneity in telomere length of human chromosomes", *Human Molecular Genetics*, 5(5):685–691 (1996).

Blasco, Maria A., et al. "Functional Characterization and Developmental Regulation of Mouse Telomerase RNA", *Science*, 269:1267–1270 (1995).

Mata, John E., et al. "A Hexameric Phosphorothioate Oligonucleotide Telomerase Inhibitor Arrests Growth of Burkitt's Lymphoma Cells in Vitro and In Vivo", *Toxicology and Applied Pharmacology*, 144:189–197 (1997).

Demidov, Vadim V. et al., "Stability of peptide nucleic acids in human serum and cellular extracts", *Biochemical Pharmacology*, 48:6 pp. 1310–1313 (1994).

Dueholm, Kim L. et al., "Synthesis of Peptide Nucleic Acid Monomers Containing the Four Natural Nucleobases: Thymine, Cytosine, Adenine, and Guanine and Their Oligomerization", *J. Org. Chem.*, 59:5767–5773 (1994).

Egholm, Michael et al., "PNA hybridizes to complementary oligonucleotides obeying the Watson rick hydrogen–bonding rules", *Nature*, 365:566–568 (1993).

Feng, Junli et al., "The RNA Component of Human Telomerase", *Science*, 269:1236–1241 (1995).

Hanvey, Jeffery C. et al., "Antisense and Antigene Properties of Peptide Nucleic Acids", *Science*, 258:1481–1485 (1992).

Nielsen, Peter E. et al., "Sequence–Selective Recognition of DNA by Strand Displacement with a Thymine–Substituted Polyamide", *Science*, 254:1497–1500 (1991).

Shippen–Lentz, Dorothy and Blackburn, Elizabeth H., "Functional Evidence for an RNA Template in Telomerase", *Science*, 247:546–552 (1990).

Thompson, Stephen A. et al., "Fmoc Mediated Synthesis of Peptide Nucleic Acids", *Tetrahedron*, 51:22 pp. 6179–6194 (1995).

Wittung, Pernilla et al., "Phospholipid membrane permeability of peptide nucleic acid", *FEBS Letters*, 365:27–29 (1995).

Norton, James C. et al., "Inhibition of human telomerase activity by peptide nucleic acid", *Nature Biotechnology*, 14:615–619 (1996).

J.C. Norton, Jr., Peptides nucleic acids; characterization of their hybridization to deplex DNA and inhibitory effects on human telomerase activity (gene sequence), *Dissertations Abstracts Int.*, 57:4 pp. 2414, B 1996.

J.C. Norton, et al., Inhibition of human telomerase activity by peptide mucleic acids, *Chemical Abstracts* 24:23, Jun. 3, 1996.

\* cited by examiner

SEQUENCE LISTING (1) GENERAL INFORMATION:

(iii) NUMBER OF SEQUENCES: 60

(2) INFORMATION FOR SEQ ID NO:1:

(i) SEQUENCE CHARACTERISTICS:
      (A) LENGTH: 13 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "peptide nucleic acid (PNA),
         where (deoxy(ribose-phosphate linkages are replaced by
         N-(2-aminoethyl)glycine units linked to nucleotide bases
         via glycine amino N through a methylenecarbonyl linker"

(xi) SEQUENCE DESCRIPTION: SEQ ID NO:1:

CAGTTAGGGT TAG                                        13

(2) INFORMATION FOR SEQ ID NO:2:

(i) SEQUENCE CHARACTERISTICS:
      (A) LENGTH: 15 base pairs
      (B) TYPE: nucleic acid (C) STRANDEDNESS: single
            (D) TOPOLOGY: linear (ii) MOLECULE TYPE: other nucleic acid
            (A) DESCRIPTION: /desc = "peptide nucleic acid (PNA),
                where (deoxy(ribose-phosphate linkages are replaced by
                N-(2-aminoethyl)glycine units linked to nucleotide bases
                via glycine amino N through a methylenecarbonyl linker"

(xi) SEQUENCE DESCRIPTION: SEQ ID NO:2:

CTCAGTTAGG GTTAG                                                                15

(2) INFORMATION FOR SEQ ID NO:3:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "peptide nucleic acid (PNA),
                where (deoxy(ribose-phosphate linkages are replaced by
                N-(2-aminoethyl)glycine units linked to nucleotide bases
                via glycine amino N through a methylenecarbonyl linker"

(xi) SEQUENCE DESCRIPTION: SEQ ID NO:3:

GGGTTAGACA A                                                                    11

(2) INFORMATION FOR SEQ ID NO:4:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "peptide nucleic acid (PNA),
                where (deoxy(ribose-phosphate linkages are replaced by
                N-(2-aminoethyl)glycine units linked to nucleotide bases
                via glycine amino N through a methylenecarbonyl linker"

(xi) SEQUENCE DESCRIPTION: SEQ ID NO:4:

TAGGGTTAGA CAA                                                                  13

(2) INFORMATION FOR SEQ ID NO:5:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "peptide nucleic acid (PNA),
                where (deoxy(ribose-phosphate linkages are replaced by
                N-(2-aminoethyl)glycine units linked to nucleotide bases
                via glycine amino N through a methylenecarbonyl linker"

(xi) SEQUENCE DESCRIPTION: SEQ ID NO:5:

GTTAGGGTTA GACAA                                                                15

(2) INFORMATION FOR SEQ ID NO:6:

(i) SEQUENCE CHARACTERISTICS:
            (A) LENGTH: 9 base pairs
            (B) TYPE: nucleic acid
            (C) STRANDEDNESS: single
            (D) TOPOLOGY: linear (ii) MOLECULE TYPE: other nucleic acid
    (A) DESCRIPTION: /desc = "peptide nucleic acid (PNA),
        where (deoxy(ribose-phosphate linkages are replaced by
        N-(2-aminoethyl)glycine units linked to nucleotide bases
        via glycine amino N through a methylenecarbonyl linker"

(xi) SEQUENCE DESCRIPTION: SEQ ID NO:6:

TAGGGTTAG                                                            9

(2) INFORMATION FOR SEQ ID NO:7:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(xi) SEQUENCE DESCRIPTION: SEQ ID NO:7:

TTAGGGTTAG                                                           10

(2) INFORMATION FOR SEQ ID NO:8:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(xi) SEQUENCE DESCRIPTION: SEQ ID NO:8:

AGTTAGGGTT AG                                                        12

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(xi) SEQUENCE DESCRIPTION: SEQ ID NO:9:

CCCTTCTCAG TTAGGGTT                                                  18

(2) INFORMATION FOR SEQ ID NO:10:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
    (A) DESCRIPTION: /desc = "peptide nucleic acid (PNA),
        where (deoxy(ribose-phosphate linkages are replaced by
        N-(2-aminoethyl)glycine units linked to nucleotide bases
        via glycine amino N through a methylenecarbonyl linker"

(xi) SEQUENCE DESCRIPTION: SEQ ID NO:10:

TAGGGTTAGA C                                                             11

(2) INFORMATION FOR SEQ ID NO:11:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..10
        (D) OTHER INFORMATION: /note= "template region of the RNA
            component of human telomerase (hTR)"

(xi) SEQUENCE DESCRIPTION: SEQ ID NO:11:

CTAACCCTAA                                                               10

(2) INFORMATION FOR SEQ ID NO:12:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(xi) SEQUENCE DESCRIPTION: SEQ ID NO:12:

GTTAGGGTTA GAC                                                           13

(2) INFORMATION FOR SEQ ID NO:13:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(xi) SEQUENCE DESCRIPTION: SEQ ID NO:13:

GTTAGGGTTA G                                                             11

(2) INFORMATION FOR SEQ ID NO:14:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "peptide nucleic acid (PNA),
                where (deoxy(ribose-phosphate linkages are replaced by
                N-(2-aminoethyl)glycine units linked to nucleotide bases
                via glycine amino N through a methylenecarbonyl linker"

(xi) SEQUENCE DESCRIPTION: SEQ ID NO:14:

CTCAGTTAGG G                                                                11

(2) INFORMATION FOR SEQ ID NO:15:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(xi) SEQUENCE DESCRIPTION: SEQ ID NO:15:

GTTAGGGT                                                                     8

(2) INFORMATION FOR SEQ ID NO:16:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(xi) SEQUENCE DESCRIPTION: SEQ ID NO:16:

AGTTAGGGT                                                                    9

(2) INFORMATION FOR SEQ ID NO:17:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(xi) SEQUENCE DESCRIPTION: SEQ ID NO:17:

CAGTTAGGGT                                                                  10

(2) INFORMATION FOR SEQ ID NO:18:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(ix) FEATURE:
        (A) NAME/KEY: modified_base
        (B) LOCATION: 1
        (D) OTHER INFORMATION: /mod_base= OTHER
            /note= "N = peptide nucleic acid nucleobase G linked to
            the carboxy end of the peptide NH-2-GlyGlyArgGlnIleLysIle
            TrpPheGlnAsnArgArgMetLysTrpLysLys"

(xi) SEQUENCE DESCRIPTION: SEQ ID NO:18:

NTTAGGGTTA G                                                            11

(2) INFORMATION FOR SEQ ID NO:19:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(ix) FEATURE:
        (A) NAME/KEY: modified_base
        (B) LOCATION: 11
        (D) OTHER INFORMATION: /mod_base= OTHER
            /note= "N = peptide nucleic acid nucleobase G linked to
            the amino end of the peptide
            GlyGlyArgGlnIleLysIleTrpPheGlnAsnArgArgMetLysTrpLysLys-
            COOH"

(xi) SEQUENCE DESCRIPTION: SEQ ID NO:19:

GTTAGGGTTA N                                                            11

(2) INFORMATION FOR SEQ ID NO:20:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:20:

Gly Gly Arg Gln Ile Lys Ile Trp Phe Gln Asn Arg Arg Met Lys Trp
1               5                   10                  15

Lys Lys (2) INFORMATION FOR SEQ ID NO:21:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy)ribose-phosphate linkages are replaced by
            N-(2-aminoethyl)glycine units linked to nucleotide bases
            via glycine amino N through a methylenecarbonyl linker"

```
        (ix) FEATURE:
              (A) NAME/KEY: modified_base
              (B) LOCATION: 1
              (D) OTHER INFORMATION: /mod_base= OTHER
                   /note= "N = peptide nucleic acid nucleobase C linked to
                   the carboxy end of the amino acid Gly"

(ix) FEATURE:
              (A) NAME/KEY: modified_base
              (B) LOCATION: 10
              (D) OTHER INFORMATION: /mod_base= OTHER
                   /note= "N = peptide nucleic acid nucleobase T linked to
                   the amino end of the amino acid Lys"

(xi) SEQUENCE DESCRIPTION: SEQ ID NO:21:

NAGTTAGGGN                                                                          10

(2) INFORMATION FOR SEQ ID NO:22:

(i) SEQUENCE CHARACTERISTICS:
              (A) LENGTH: 981 base pairs
              (B) TYPE: nucleic acid
              (C) STRANDEDNESS: single
              (D) TOPOLOGY: linear (ii) MOLECULE TYPE: DNA (genomic)

(ix) FEATURE:
              (A) NAME/KEY: misc_RNA
              (B) LOCATION: 266..716
              (D) OTHER INFORMATION: /product= "hTR"
                   /note= "RNA component of human telomerase (hTR)"

(ix) FEATURE:
              (A) NAME/KEY: -
              (B) LOCATION: 1..981
              (D) OTHER INFORMATION: /note= "PstI fragment of
                   SauIIIA1-HindIII fragment of clone 28-1"

(xi) SEQUENCE DESCRIPTION: SEQ ID NO:22:

CTGCAGAGGA TAGAAAAAAG WCCCTCTGAT ACCTCAAGTT AGTTTCACCT TTAAAGAAGG        60

TCGGAAGTAA AGACGCAAAG CCTTTCCCGG ACGTGCGGAA GGGCAACGTC CTTCCTCATG       120

GCCGGAAATG GAACTTTAAT TTCCCGTTCC CCCCAACCAG CCCGCCCGAG AGAGTGACTC       180

TCACGAGAGC CGCGAGAGTC AGCTTGGCCA ATCCGTGCGG TCGGCGGCCG CTCCCTTTAT       240

AAGCCGACTC GCCCGGCAGC GCACCGGGTT GCGGAGGGTG GGCCTGGGAG GGGTGGTGGC       300

CATTTTTTGT CTAACCCTAA CTGAGAAGGG CGTAGGCGCC GTGCTTTTGC TCCCCGCGCG       360

CTGTTTTTCT CGCTGACTTT CAGCGGGCGG AAAAGCCTCG GCCTGCCGCC TTCCACCGTT       420

CATTCTAGAG CAAACAAAAA ATGTCAGCTG CTGGCCCGTT CGCCCCTCCC GGGGACCTGC       480

GGCGGGTCGC CTGCCCAGCC CCCGAACCCC GCCTGGAGGC CGCGGTCGGC CCGGGGCTTC       540

TCCGGAGGCA CCCACTGCCA CCGCGAAGAG TTGGGCTCTG TCAGCCGCGG GTCTCTCGGG       600

GGCGAGGGCG AGGTTCAGGC CTTTCAGGCC GCAGGAAGAG GAACGGAGCG AGTCCCCGCG       660

CGCGGCGCGA TTCCCTGAGC TGTGGGACGT GCACCCAGGA CTCGGCTCAC ACATGCAGTT       720

CGCTTTCCTG TTGGTGGGGG GAACGCCGAT CGTGCGCATC CGTCACCCCT CGCCGGCAGT       780

GGGGGCTTGT GAACCCCCAA ACCTGACTGA CTGGGCCAGT GTGCTGCAAA TTGGCAGGAG       840

ACGTGAAGGC ACCTCCAAAG TCGGCCAAAA TGAATGGGCA GTGAGCCGGG GTTGCCTGGA       900

GCCGTTCCTG CGTGGGTTCT CCCGTCTTCC GCTTTTTGTT GCCTTTATG GTTGTATTAC        960

AACTTAGTTC CTGCTCTGCA G                                                 981
```

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "TS primer"

(xi) SEQUENCE DESCRIPTION: SEQ ID NO:23:

AATCCGTCGA GCAGAGTT                                                        18

(2) INFORMATION FOR SEQ ID NO:24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..24
        (D) OTHER INFORMATION: /note= "CX reverse primer"

(xi) SEQUENCE DESCRIPTION: SEQ ID NO:24:

CCCTTACCCT TACCCTTACC CTAA                                      24

(2) INFORMATION FOR SEQ ID NO:25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(xi) SEQUENCE DESCRIPTION: SEQ ID NO:25:

TTTGTCTAAC CCTAACTGAG AAGG                                      24

(2) INFORMATION FOR SEQ ID NO:26:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(xi) SEQUENCE DESCRIPTION: SEQ ID NO:26:

CCATTTTTTG TCTAACCCTA ACT                                        23

(2) INFORMATION FOR SEQ ID NO:27:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(xi) SEQUENCE DESCRIPTION: SEQ ID NO:27:

TAACTGAGAA GGGCGT       16

(2) INFORMATION FOR SEQ ID NO:28:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(xi) SEQUENCE DESCRIPTION: SEQ ID NO:28:

ACCCTAACTG AGAAG       15

(2) INFORMATION FOR SEQ ID NO:29:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(xi) SEQUENCE DESCRIPTION: SEQ ID NO:29:

ACCCTAACTG       10

(2) INFORMATION FOR SEQ ID NO:30:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(xi) SEQUENCE DESCRIPTION: SEQ ID NO:30:

ACCCTAAC       8

(2) INFORMATION FOR SEQ ID NO:31:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(xi) SEQUENCE DESCRIPTION: SEQ ID NO:31:

CTAACCCTAA C                                                          11

(2) INFORMATION FOR SEQ ID NO:32:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(xi) SEQUENCE DESCRIPTION: SEQ ID NO:32:

CTAACTCTAA C                                                          11

(2) INFORMATION FOR SEQ ID NO:33:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(xi) SEQUENCE DESCRIPTION: SEQ ID NO:33:

GCCCTTCTCA G                                                          11

(2) INFORMATION FOR SEQ ID NO:34:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(ix) FEATURE:
        (A) NAME/KEY: modified_base
        (B) LOCATION: 1
        (D) OTHER INFORMATION: /mod_base= OTHER
            /note= "N = 1-50 peptide nucleic acid nucleobases,
            selected from U, T, A, G, i or C"

-continued

```
    (ix) FEATURE:
        (A) NAME/KEY: modified_base
        (B) LOCATION: 8
        (D) OTHER INFORMATION: /mod_base= OTHER
            /note= "N = 1-50 peptide nucleic acid nucleobases,
            selected from U, T, A, G, i or C"

(xi) SEQUENCE DESCRIPTION: SEQ ID NO:34:

NTTAGGGN                                                                        8

(2) INFORMATION FOR SEQ ID NO:35:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(ix) FEATURE:
        (A) NAME/KEY: modified_base
        (B) LOCATION: 1
        (D) OTHER INFORMATION: /mod_base= OTHER
            /note= "N = 1-50 peptide nucleic acid nucleobases,
            selected from U, T, A, G, i or C"

(ix) FEATURE:
        (A) NAME/KEY: modified_base
        (B) LOCATION: 8
        (D) OTHER INFORMATION: /mod_base= OTHER
            /note= "N = 1-50 peptide nucleic acid nucleobases,
            selected from U, T, A, G, i or C"

(xi) SEQUENCE DESCRIPTION: SEQ ID NO:35:

NTAGGGTN                                                                        8

(2) INFORMATION FOR SEQ ID NO:36:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(ix) FEATURE:
        (A) NAME/KEY: modified_base
        (B) LOCATION: 1
        (D) OTHER INFORMATION: /mod_base= OTHER
            /note= "N = 1-50 peptide nucleic acid nucleobases,
            selected from U, T, A, i or C"

(ix) FEATURE:
        (A) NAME/KEY: modified_base
        (B) LOCATION: 8
        (D) OTHER INFORMATION: /mod_base= OTHER
            /note= "N = 1-50 peptide nucleic acid nucleobases,
            selected from U, T, A, i or C"

(xi) SEQUENCE DESCRIPTION: SEQ ID NO:36:

NAGGGTTN                                                                        8
```

```
(2) INFORMATION FOR SEQ ID NO:37:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(ix) FEATURE:
        (A) NAME/KEY: modified_base
        (B) LOCATION: 1
        (D) OTHER INFORMATION: /mod_base= OTHER
            /note= "N = 1-50 peptide nucleic acid nucleobases,
            selected from U, T, A, G, i or C"

(xi) SEQUENCE DESCRIPTION: SEQ ID NO:37:

NGGGTTAN                                                                      8

(2) INFORMATION FOR SEQ ID NO:38:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(ix) FEATURE:
        (A) NAME/KEY: modified_base
        (B) LOCATION: 1
        (D) OTHER INFORMATION: /mod_base= OTHER
            /note= "N = 1-50 peptide nucleic acid nucleobases,
            selected from U, T, A, G, i or C"

(ix) FEATURE:
        (A) NAME/KEY: modified_base
        (B) LOCATION: 8
        (D) OTHER INFORMATION: /mod_base= OTHER
            /note= "N = 1-50 peptide nucleic acid nucleobases,
            selected from U, T, A, G, i or C"

(xi) SEQUENCE DESCRIPTION: SEQ ID NO:38:

NGGTTAGN                                                                      8

(2) INFORMATION FOR SEQ ID NO:39:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(ix) FEATURE:
        (A) NAME/KEY: modified_base
        (B) LOCATION: 1
        (D) OTHER INFORMATION: /mod_base= OTHER
            /note= "N = 1-50 peptide nucleic acid nucleobases,
            selected from U, T, A, G, i or C"
```

(ix) FEATURE:
            (A) NAME/KEY: modified_base
            (B) LOCATION: 8
            (D) OTHER INFORMATION: /mod_base= OTHER
                /note= "N = 1-50 peptide nucleic acid nucleobases,
                selected from U, T, A, G, i or C"

(xi) SEQUENCE DESCRIPTION: SEQ ID NO:39:

NGTTAGGN                                                                     8

(2) INFORMATION FOR SEQ ID NO:40:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:40:

UUUGUCUAAC CCUAACUGAG AAGGG                                                 25

(2) INFORMATION FOR SEQ ID NO:41:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(xi) SEQUENCE DESCRIPTION: SEQ ID NO:41:

CCCTTCTCAG TTAGGGTTAG                                                       20

(2) INFORMATION FOR SEQ ID NO:42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(xi) SEQUENCE DESCRIPTION: SEQ ID NO:42:

AGGATCTTCA CCTAGATCCT                                                       20

(2) INFORMATION FOR SEQ ID NO:43:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

```
   (xi) SEQUENCE DESCRIPTION: SEQ ID NO:43:

TGTAAGGAAC TAG                                                          13

(2) INFORMATION FOR SEQ ID NO:44:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate (PS)
            nucleic acid"

(xi) SEQUENCE DESCRIPTION: SEQ ID NO:44:

GTTAGGGTTA G                                                            11

(2) INFORMATION FOR SEQ ID NO:45:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate (PS)
            nucleic acid"

(xi) SEQUENCE DESCRIPTION: SEQ ID NO:45:

CTCAGTTAGG GTTAG                                                        15

(2) INFORMATION FOR SEQ ID NO:46:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate (PS)
            nucleic acid"

(xi) SEQUENCE DESCRIPTION: SEQ ID NO:46:

TAGGGTTAGA CAA                                                          13

(2) INFORMATION FOR SEQ ID NO:47:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate (PS)
            nucleic acid"

(xi) SEQUENCE DESCRIPTION: SEQ ID NO:47:

AGGATCTTCA CCTAGATCCT                                                   20

(2) INFORMATION FOR SEQ ID NO:48:

(i) SEQUENCE CHARACTERISTICS:
        (A) LENGTH: 13 base pairs
        (B) TYPE: nucleic acid
```

```
            (C) STRANDEDNESS: single
            (D) TOPOLOGY: linear (ii) MOLECULE TYPE: other nucleic acid
            (A) DESCRIPTION: /desc = "phosphorothioate (PS)
                nucleic acid"

(xi) SEQUENCE DESCRIPTION: SEQ ID NO:48:

TGTAAGGAAC TAG                                                          13

(2) INFORMATION FOR SEQ ID NO:49:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: RNA (genomic)

(xi) SEQUENCE DESCRIPTION: SEQ ID NO:49:

UUUUGUCUAA CCCUAACUGA GAAGGGCGUA G                                      31

(2) INFORMATION FOR SEQ ID NO:50:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "peptide nucleic acid (PNA),
                where (deoxy(ribose-phosphate linkages are replaced by
                N-(2-aminoethyl)glycine units linked to nucleotide bases
                via glycine amino N through a methylenecarbonyl linker"

(xi) SEQUENCE DESCRIPTION: SEQ ID NO:50:

TAGACCAAAA AATG                                                         14

(2) INFORMATION FOR SEQ ID NO:51:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "peptide nucleic acid (PNA),
                where (deoxy(ribose-phosphate linkages are replaced by
                N-(2-aminoethyl)glycine units linked to nucleotide bases
                via glycine amino N through a methylenecarbonyl linker"

(xi) SEQUENCE DESCRIPTION: SEQ ID NO:51:

GTTAGACAAA AAA                                                          13

(2) INFORMATION FOR SEQ ID NO:52:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "peptide nucleic acid (PNA),
                where (deoxy(ribose-phosphate linkages are replaced by
                N-(2-aminoethyl)glycine units linked to nucleotide bases
                via glycine amino N through a methylenecarbonyl linker"
```

(xi) SEQUENCE DESCRIPTION: SEQ ID NO:52:

GGTTAGACAA AAA                                                                    13

(2) INFORMATION FOR SEQ ID NO:53:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(xi) SEQUENCE DESCRIPTION: SEQ ID NO:53:

TCTCAGTTAG G                                                                      11

(2) INFORMATION FOR SEQ ID NO:54:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(xi) SEQUENCE DESCRIPTION: SEQ ID NO:54:

TTCTCAGTTA G                                                                      11

(2) INFORMATION FOR SEQ ID NO:55:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(xi) SEQUENCE DESCRIPTION: SEQ ID NO:55:

CCCTTCTCAG TTA                                                                    13

(2) INFORMATION FOR SEQ ID NO:56:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy(ribose-phosphate linkages are replaced by
            N-(2-aminoethyl)glycine units linked to nucleotide bases
            via glycine amino N through a methylenecarbonyl linker"

(xi) SEQUENCE DESCRIPTION: SEQ ID NO:56:

CGCCCTTCTC AGT                                                                    13

(2) INFORMATION FOR SEQ ID NO:57:

(i) SEQUENCE CHARACTERISTICS:
       (A) LENGTH: 11 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "peptide nucleic acid (PNA),
           where (deoxy(ribose-phosphate linkages are replaced by
           N-(2-aminoethyl)glycine units linked to nucleotide bases
           via glycine amino N through a methylenecarbonyl linker"

(xi) SEQUENCE DESCRIPTION: SEQ ID NO:57:

CCCTTCTCAG T                                                           11

(2) INFORMATION FOR SEQ ID NO:58:

(i) SEQUENCE CHARACTERISTICS:
       (A) LENGTH: 11 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "peptide nucleic acid (PNA),
           where (deoxy(ribose-phosphate linkages are replaced by
           N-(2-aminoethyl)glycine units linked to nucleotide bases
           via glycine amino N through a methylenecarbonyl linker"

(xi) SEQUENCE DESCRIPTION: SEQ ID NO:58:

CGCCCTTCTC A                                                           11

(2) INFORMATION FOR SEQ ID NO:59:

(i) SEQUENCE CHARACTERISTICS:
       (A) LENGTH: 11 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "peptide nucleic acid (PNA),
           where (deoxy(ribose-phosphate linkages are replaced by
           N-(2-aminoethyl)glycine units linked to nucleotide bases
           via glycine amino N through a methylenecarbonyl linker"

(xi) SEQUENCE DESCRIPTION: SEQ ID NO:59:

GTTAGAGTTA G                                                           11

(2) INFORMATION FOR SEQ ID NO:60:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: RNA (genomic)

(xi) SEQUENCE DESCRIPTION: SEQ ID NO:60:

GUCUAACCCU AACUGAGAA                                                   19

INHIBITION OF MAMMALIAN TELOMERASE BY PEPTIDE NUCLEIC ACIDS

CROSS-REFERENCE TO RELATED APPLICATIONS

The present application is a continuation of U.S. application Ser. No. 08/838,545, filed on Apr. 9, 1997 now U.S. Pat. No. 6,046,307, which is a continuation-in-part application of U.S. application Ser. No. 08/630,019, filed Apr. 9, 1996, now U.S. Pat. No. 6,015,710.

FEDERALLY SPONSORED RESEARCH OR DEVELOPMENT

Not applicable.

FIELD OF THE INVENTION

The invention relates to peptide nucleic acids and to methods for using them to inhibit and detect mammalian telomerase.

BACKGROUND OF THE INVENTION

A. Non-Phosphodiester Polynucleotide Analogs

DNA consists of covalently linked units, each composed of a nucleobase (adenine, cytosine, guanine, or thymine) attached to a pentose sugar (deoxyribose) via a glycosidic linkage, with a phosphate ester (phosphodiester) linking successive sugar rings. Numerous types of DNA analogs have been synthesized, with most variations typically having a modification or replacement of the phosphodiester backbone.

Examples of polynucleotide analogs having a modified phosphate backbone include: methylphosphonates, phosphorothioates, phosphoramidites, phosphorodithioates, phosphorotriesters, and boranophosphates. An alternative approach is the development of structural mimetics of the phosphodiester linkage, generally with the objective of providing a backbone linkage that is charge neutral (to increase the stability of DNA hybrid complexes), relatively hydrophobic (to increase cellular uptake), and achiral. Examples of polynucleotide analogs wherein the phosphodiester backbone is replaced by a structural mimic linkage include: alkanes, ethers, thioethers, amines, ketones, formacetals, thioformacetals, amides, carbamates, ureas, hydroxylamines, sulfamates, sulfamides, sulfones, glycinylamides, and others.

In addition to replacing the phosphodiester linkage, alternative approaches have replaced the entire (deoxy)ribose-phosphate backbone, retaining just the nucleobases. One of these approaches replaces the entire (deoxy)ribose-phosphate backbone with a peptide-like backbone, generating a so-called "peptide nucleic acid," "polyamide nucleic acid," or simply "PNA" (Nielsen et al. (1991) Science 254: 1497; Nielsen et al. (1994) Bioconj. Chem. 5: 3; Leijon et al. (1994) Biochemistry 33: 9820; Huang et al. (1991) J. Org. Chem. 56: 6007; Egholm et al. (1993) Nature 365: 556; Buchardt et al. (1993) Trends Biotechnol. 11; 384; Nielsen P E (1995) Rev Biophys Biomol Struct 24: 167; Agrawal et al. (1995) Curr Opin Biotechnol. 6: 12; Nielsen et al. (1993) Anticancer Drug Res. 8: 53; Cook P D (1991) Anticancer Drug Des. 6: 585). PNAs have an achiral, noncharged backbone, as exemplified by a backbone composed of N-(2-aminoethyl)glycine units, which is a suitable structural mimic of DNA. Hybrids between such a PNA and complementary sequence DNA or RNA are reported to exhibit higher thermal stability per base pair than DNA:DNA or RNA:RNA duplexes (Wittung et al. Nature 368: 561).

PNAs have been reported to have many interesting properties. Binding of PNA to double-stranded DNA occurs by strand invasion via formation of a D-loop strand displacement complexes (Egholm et al. (1993) Nature 365: 556) that have unique biological properties, including the capacity to serve as artificial transcription promoters in some contexts (Mollegaard et al. (1994) Proc. Natl. Acad. Sci. (U.S.A.) 91: 3892). PNAs have been shown to bind to DNA and RNA in a sequence-dependent manner (Brown et al. (1994) Science 265: 777; Egholm et al. (1993) op. cit), and exhibit superior base pair mismatch discrimination in PNA/DNA hybrids than do DNA/DNA duplexes (Orum et al. (1993) Nucleic Acids Res 21: 5332).

PNAs have been used to target the single strand-specific nuclease S1 to a PNA/DNA hybrid formed via strand invasion, making S1 nuclease act like a pseudo restriction enzyme (Demidov et al. (1993) Nucleic Acids Res 21: 2103). Alternatively, complementary PNAs have been used to block sequence-specific DNA restriction enzyme cleavage of dsDNA plasmids (Nielsen et al. (1993) Nucleic Acids Res 21: 197). PNAs have been used to arrest transcription elongation by targeting a complementary sequence PNA to the template DNA strand (Nielsen et al. (1994) Gene 149: 139). PNA strand invasion has also been shown to inhibit transcriptional activation by the transcription factor NF-κB by blocking its interaction with 5' regulatory sequences to which it normally binds (Vickers et al. (1995) Nucleic Acids Res 23: 3003). Interaction of certain DNA-binding ligands with PNA/DNA hybrids has also been reported (Wittung et al. (1994) Nucleic Acids Res 22: 5371).

The antisense and antigene properties of PNAs have been reported (Bonham et al. (1995) Nucleic Acids Res 23: 1197; Hanvey et al. (1992) Science 258: 1481; Nielsen et al. (1993) AntiCancer Drug Des 8: 53). A vector-mediated delivery method for introducing PNAs through phospholipid membranes and through the blood-brain barrier have been reported (Pardridge et al. (1995) Proc. Natl. Acad. Sci. (U.S.A.) 92: 5592; Wittung et al. (1995) FEBS Lett 375: 27). Orum et al. (1995) Biotechniques 19: 472 report a method for sequence-specific purification of nucleic acids by PNA-controlled hybrid selection.

B. Telomerase and Telomerase-Related Proteins

The DNA at the ends of telomeres of the chromosomes of eukaryotes usually consists of tandemly repeated simple sequences. Telomerase is a ribonucleoprotein enzyme that synthesizes one strand of the telomeric DNA using as a template an 11 nucleotide sequence contained within the RNA component of the enzyme (see Blackburn (1992) Annu. Rev. Biochem. 61:113–129). The RNA component of human telomerase has been cloned and sequenced (Feng et al. (1995) Science 269: 1267 and U.S. Pat. No. 5,583,016).

Despite the seemingly simple nature of the repeat units of telomeric DNA, scientists have long known that telomeres have an important biological role in maintaining chromosome structure and function. More recently, evidence consistent with a loss of telomeric DNA acting as a trigger of cellular senescence and aging indicates that regulation of telomerase may have important biological implications. (see Harley (1991) Mutation Research 256: 271–282). In addition, telomerase activity is detected in 85–95% of human tumors, and is required for sustained tumor proliferation. Maintenance of telomere length in tumor cell lines can be prevented by the expression of antisense RNA complementary to the hTR, leading to cell crisis (Feng et al. (1995) Science 269: 1236), and telomerase inhibition is believed to suppress tumor growth.

Methods for detecting telomerase activity, as well as for identifying compounds that regulate or affect telomerase activity, together with methods for diagnosing of cellular senescence and immortalization by controlling telomere length and telomerase activity, have been described. See International Patent Application Publication Nos. WO 95/13381; WO 95/13382; and WO 93/23572. Polynucleotide primers and probes that specifically hybridize to the RNA component of mammalian telomerase are also described in U.S. Pat. No. 5,583,016; U.S. patent application Ser. Nos: 08/272,102, filed Jul. 7, 1994; 08/472,802, filed Jun. 7, 1995; 08/482,115, filed Jun. 7, 1995; 08/521,634, filed Aug. 31, 1995; 08/630,019, filed Apr. 9, 1996; 08/660,678, filed Jun. 5, 1996; and International Patent Application Publication No. WO 96/01835. Such polynucleotides can be used to detect the RNA component of telomerase and inhibit telomerase activity, particularly in cancer cells. For example, DNA oligonucleotides can inhibit telomerase, but this inhibition requires that oligonucleotides be relatively long (18–40 nucleotides) and be present at relatively high concentrations (Collins et al. (1995) *Cell* 81: 677; Shippen-Lentz and Blackburn (1990) *Science* 247: 546).

SUMMARY OF THE INVENTION

The uncharged nature of the PNA backbone increases the melting temperature of associating strands, increases the rate of association with targeted nucleic acids, and affords greater resistance to degradation by proteases or nucleases. These characteristics provide high affinity and enhanced rates of association with the target polynucleotide. Accordingly, PNAs are useful as probes to detect the RNA compoment of mammalian telomerase and as inhibitors of telomerase activity.

In an effort to develop highly efficient telomerase inhibitors that combine chemical stability with efficient and selective inhibition, the inhibition of human telomerase was examined by modified PNAs that are known to be nuclease-resistant. To this end, inhibition of telomerase activity was assayed with PNA polynucleotides that specifically hybridized to the template region of the RNA component of telomerase. Such PNAs provided efficient inhibition of telomerase activity.

In one aspect, the invention provides a peptide nucleic acid ("PNA") comprising a sequence of six to twenty-five nucleotides that specifically hybridizes to an RNA component of mammalian telomerase, wherein the sequence comprises GGG that specifically hybridizes to the template region of the RNA component of mammalian telomerase.

In one embodiment, the PNA includes the sequence GTTAGGG that specifically hybridizes to the template region; and in a further embodiment the PNA includes the sequence AGTTAGGG that specifically hybridizes to the template region. In yet a further embodiment, the PNA has a sequence of no more than 25 nucleotides.

In one embodiment, the PNA comprises an amino terminus and a carboxy terminus, where the termini further comprise at least one amino terminal amine or amino acid and at least on carboxy terminal carboxylate or amino acid.

In one embodiment, the amino-terminus of the PNA comprises an N-linked substituent, such as acetyl, benzoic acid, retenoic acid, cholesterol derivative, and the like. The amino terminus can alternatively or in addition comprise one or more amino or imino acids (e.g., Pro, Tyr, Phe, Gly, Lys, Ser, Cys), generally linked via a peptide bond to the amine nitrogen of the PNA sequence, and/or a linked polynucleoticle sequence.

In another embodiment, the carboxy-terminus of the PNA comprises a polypeptide, amino acid, nucleotide, or polynucleotide, generally linked to the carboxylate via an ester or other carbonyl bond (e.g., peptide bond for linked amino acid). As an example, the carboxy-terminus can comprise a moiety having a thiol group suitable for forming disulfide, thioether, or thioester linkages, such as with other thiol-containing molecules (e.g., a Cys-containing polypeptide), nucleotides capable of forming thioether or thioester linkages, and the like.

In another embodiment, the PNA comprises a linked hydrophobic moiety (e.g., a cholesterol derivative or fatty acyl chain) for enhanced cell uptake and/or liposomal formulation.

In one embodiment, the PNA has a polynucleotide sequence-$N_x$TTAGGGN$_y$-, -$N_x$TAGGGTN$_y$-, -$N_x$AGGGTTN$_y$-, -$N_x$GGGTTAN$_y$-, -$N_x$GGTTAGN$_y$-, or -$N_x$GTTAGGN$_y$-, wherein $N_x$ and $N_y$ are each a sequence of 1–50 nucleotides and wherein the nucleotides are selected from uridine, thymine, adenine, guanine, inosine, and cytosine.

In another embodiment, the PNA further comprises from 1 to 10,000 covalently linked nucleotides, and in another embodiment the PNA further comprises from 1 to 10,000 covalently linked amino acids.

In another embodiment, the PNA comprises a sequence selected from: CAGTTAGGGTTAG (SEQ ID NO:1); CTCAGTTAGGGTTAG (SEQ ID NO:2); GGGTTAGACAA (SEQ ID NO:3); TAGGGTTAGACAA (SEQ ID NO:4); GTTAGGGTTAGACAA (SEQ ID NO:5); TAGGGTTAG (SEQ ID NO:6); TTAGGGTTAG (SEQ ID NO:7); AGTTAGGGTTAG (SEQ ID NO:8); CCCTCTCAGTTAGGGTT (SEQ ID NO:9); TAGGGTTAGAC (SEQ ID NO:10); GGGTTAGACAA (SEQ ID NO:11); GTTAGGGTTAGAC (SEQ ID NO:12); GTTAGGGTTAG (SEQ ID NO:13); CTCAGTTAGGG (SEQ ID NO:14); GTTAGGGT (SEQ ID NO:15); AGTTAGGGT (SEQ ID NO: 16); and CAGTTAGGGT (SEQ ID NO:17). In a further embodiment, the PNA is a sequence corresponding to one of these sequences listed above.

In one embodiment, the PNA comprises a polypeptide sequence that enhances cellular uptake of the PNA. In another embodiment, the polypeptide sequence is the h region of a signal peptide or the 3rd helix of Antp-HD. In a further embodiment, the PNA is: NH2-GlyGlyArgGlnIleLysIleTrpPheGlnAsnArg-ArgMetLysTrpLysLys-GTTAGGGTTAG-COOH (SEQ ID NO:18); and NH2-GTT-AGGGTTAG-GlyGlyArgGlnIleLysIleTrpPhe-GlnAsnArgArgMetLysTrpLysLys-COOH (SEQ ID NO: 19).

In one embodiment, the PNAs of the invention can be used for molecular diagnostic embodiments, such as the use of detectable, i.e., labeled, PNAs to serve as hybridization probes to detect and/or quantitate polynucleotides (e.g., mRNA or genomic DNA) having the human hTR sequence; the PNA probes are also used for forensic identification of individuals, such as for paternity testing or identification of criminal suspects or unknown decedents based on their hTR gene RFLP pattern.

In another aspect, the invention provides a composition comprising a PNA and an excipient or delivery vehicle. In one embodiment, the delivery vehicle is a liposome formulation. In another embodiment the PNA of the composition has a sequence according to those listed above.

In one embodiment, the invention provides pharmaceutical compositions comprising these therapeutic PNA species, alone, in combination with each other or other therapeutic agents, and/or together with a pharmaceutically acceptable carrier or salt, which may include formulation in a lipofection complex, liposome, or immunoliposome for targeted delivery of the therapeutic PNA agent. The invention also provides combinations of such therapeutic PNAs with other pharmaceuticals, such as antineoplastic agents and other cytotoxic or cytostatic agents; antifungal agents (e.g., for treatment of AIDS patients); nucleotides; and other pharmaceutical agents suitable for treating disease conditions such as neoplasia, hyperplasia, HIV-infection/AIDS and associated pathologies, and other diseases characterized by abnormal telomere metabolism or telomerase activity.

The invention provides PNA therapeutic agents that inhibit neoplasia or apoptosis by modulating telomerase function by mimicking or inhibiting telomerase RNA component; such therapeutic PNAs can be used as pharmaceuticals as well as commercial laboratory reagents. Such pharmaceuticals will be used to treat a variety of human and veterinary diseases, such as: neoplasia, hyperplasia, neurodegenerative diseases, aging, AIDS, fungal infection, and the like. In an embodiment, the PNA comprises a PNA nucleotide sequence capable of inhibiting telomerase by mimicking and/or binding to (hybridizing to) a telomerase RNA component sequence, or alternatively the PNA can serve as an enzymatically inactive telomerase RNA component that can competitively inhibit formation of functional telomerase holoenzyme.

In another aspect the invention provides a method of inhibiting mammalian telomerase activity in a mammalian cell by contacting mammalian telomerase with a PNA comprising a sequence of six to twenty-five nucleotides that specifically hybridizes to an RNA component of mammalian telomerase, wherein the sequence comprises GGG that specifically hybridizes to the template region of the RNA component of mammalian telomerase.

In further embodiments, the method incorporates the embodiments listed above.

In one embodiment, the mammalian cell is a transformed cell, and in another embodiment the mammalian cell is a human cell.

In another aspect the invention provides a method for detecting the RNA component of mammalian telomerase in a sample by: first, contacting the sample with a PNA comprising a sequence of six to twenty-five nucleotides that specifically hybridizes to an RNA component of mammalian telomerase, wherein the sequence comprises GGG that specifically hybridizes to the template region of the RNA component of mammalian telomerase and second, detecting whether the PNA has specifically hybridized to the template region. Specific hybridization provides detection of the RNA component of telomerase in the sample.

In one embodiment, the PNA has a sequence of no more than twenty-five nucleotides.

The invention provides methods for inhibiting telomerase activity within a cell or group of cells by contacting the cell(s) with a therapeutically effective amount of a telomerase modulating PNA that alters telomerase activity in that cell. Such PNAs include PNAs having a corresponding or complementary sequence to the telomerase RNA component, PNA-based ribozymes, and other PNAs capable of modulating mammalian telomerase gene activity, such as for human gene therapy.

The methods can comprise the use of a derivatized PNA capable of specifically hybridizing to a telomerase RNA component in a mammalian telomerase, wherein the derivatized PNA is delivered into mammalian cells having telomerase activity and inhibits telomerase activity by localizing to telomerase RNA component or telomerase protein component, or telomeric sequences of a chromosome, and thereby inactivating or inhibiting telomerase activity.

In another aspect the invention provides a PNA comprising a nucleotide sequence and a polypeptide sequence that translocates the PNA across the cell membrane.

In one embodiment, the polypeptide sequence is from a homeodomain protein or the h region of a signal peptide. In another embodiment, the polypeptide sequence is NH2-GlyGlyArgGlnIleLysIleTrpPheGlnAsnArgArgMetLysTrp-LysLys-COOH (SEQ ID NO:20); and NH2-GlyGlyArgGlnIleLysIleTrpPheGlnAsnArgArg-MetLysTrpLysLys-COOH (SEQ ID NO:21).

Other suitable polynucleotide sequences and variations are evident to the skilled artisan in view of the teachings of the specification and experimental examples, see, e.g., Tables 1–3, infra. Each PNA comprising a selected polynucleotide sequence variant can be conveniently and routinely assayed to determine the exact level of activity, such as the $IC_{50}$ value using the assay methods taught in the experimental examples, and PNA species having a desired level of activity at inhibiting telomerase can be chosen for further use and formulation.

Candidate PNA sequences can be identified by their ability to produce a statistically significant increase or decrease in enzymatic activity of mammalian telomerase, in either purified or unpurified form. A pool of PNA species comprising variant sequences having 1, 2, 3, 4, 5, or 6 mismatches as compared to a naturally-occurring mammalian telomerase RNA component or its complement are screened, typically over a range of varying concentrations, for their ability to produce a statistically significant increase or decrease in enzymatic activity of a mammalian telomerase (recombinant or naturally-occurring in purified or unpurified form).

In another aspect, the invention provides a method of treating cancer in a subject, comprising administering to said subject a therapeutically effective amount of a PNA described above.

Other features and advantages of the invention will be apparent from the following description of the drawings, preferred embodiments of the invention, the examples, and the claims.

DETAILED DESCRIPTION

A. Introduction

Figure 1C:
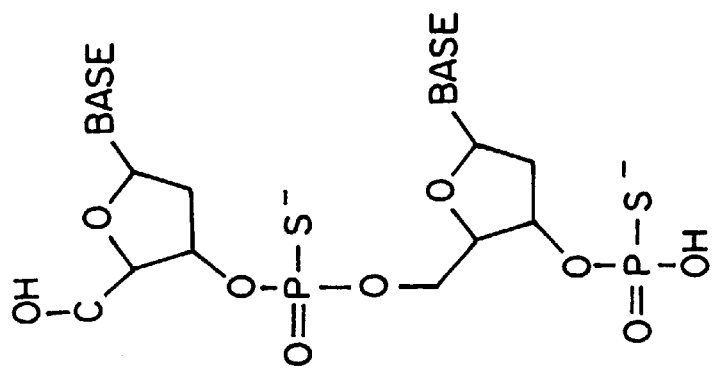
FIGS. 1A–C: Chemical structure of DNA (Panel A), PNA (Panel B), and PS (Panel C).

The nomenclature used hereafter and the laboratory procedures in cell culture, molecular genetics, and nucleic acid chemistry and hybridization described herein often involve well known and commonly employed procedures in the art. Standard techniques are used for recombinant nucleic acid methods, polynucleotide synthesis, and microbial culture and transformation (e.g., electroporation, lipofection). The techniques and procedures are generally performed according to conventional methods in the art and various general references (see generally, Sambrook et al. Molecular Cloning: A Laboratory Manual, 2d ed. (1989); Ausubel et al., *Current Protocols in Molecular Biology* (1995)).

PNAs and other synthetic nucleotide analogs can be synthesized by any art known method, including use of Applied BioSystems synthesizer equipment provided with appropriate reagents, or can be obtained by contract synthesis with a suitable custom manufacturer, such as PerSeptive Biosystems or the like.

B. Definitions

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2d ed. 1994); *The Cambridge Dictionary of Science and Technology* (Walker ed., 1988); and Hale & Marham, *The Harper Collins Dictionary of Biology* (1991). Although any methods and materials similar or equivalent to those described herein can be used in the practice or testing of the present invention, preferred methods and materials are described. As used herein, the following terms have the meanings ascribed to them unless specified otherwise.

"Telomerase" or "telomerase ribonucleoprotein complex" refers to a ribonucleoprotein enzyme of eukaryotic origin identifiable by its ability to polymerize a DNA sequence of a eukaryotic telomere. Telomerase is further characterized by an RNA component having sequences complementary to at least part of the telomeric repeat of the source species and by one or more protein components. "Mammalian telomerase" and "human telomerase" refer to telomerases that can be found naturally in various mammalian or human cells, respectively, or having polypeptide components with the same amino acid sequences, and RNA components with the same nucleotide sequences. Human telomerase contains the RNA component, "hTR." The term "telomerase" includes all allelic forms of telomerase, including wild-type and mutant forms.

"Telomerase activity" refers to the synthesis of telomeric DNA by telomerase. A preferred assay method for detecting telomerase activity is the TRAP assay (see International Application published under the PCT, WO 95/13381). This assay measures the amount of radioactive nucleotides incorporated into elongation products, polynucleotides, formed by nucleotide addition to a telomerase substrate or primer. The radioactivity incorporated can be measured as a function of the intensity of a band on a PhosphorImager™ screen exposed to a gel on which the radioactive products are separated. A test experiment and a control experiment can be compared by visually using the PhosphorImager™ screens (see also the commercially available TRAP-eze™ telomerase assay kit (Oncor); and Morin, *Cell* 59: 521–529 (1989)).

"Telomerase-related condition" refers to a condition in a subject maintained by telomerase activity within cells of the individual. Telomerase-related conditions include, e.g., cancer (telomerase-activity in malignant cells), fertility (telomerase activity in germ-line cells) and hematopoiesis (telomerase activity in hematopoietic stem cells).

The "template region" of the RNA component of mammalian telomerase refers to a subsequence of the RNA component of mammalian telomerase that serves as; a template for synthesis of telomeric repeats. All vertebrates appear to have the conserved sequence 5'-TTAGGG-3' at chromosome ends, although subtelomeric sequences can vary (see, e.g., Harley & Villeponteau, *Current Opin. in Gen. and Dev.* 5: 249–255 (1995)). The template region is complementary to at least the single telomeric repeat sequence, and can also include a second portion of the telomeric repeat sequence. For example, the template region of hTR is 5'-CTAACCCTAA-3', located at nucleotides 46–55 of hTR (311–320 on SEQ ID NO:22).

"Nucleotide" refers to the monomer units that are assembled to form a polynucleotide. This definition includes the nucleotide monomers used to form PNAS.

"Polynucleotide" refers to a polymer composed of nucleotides (ribonucleotides, deoxyribonucleotides, related naturally occurring structural variants, and synthetic non-naturally occurring analogs thereof, e.g, PNAs) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like.

Figure 1B:
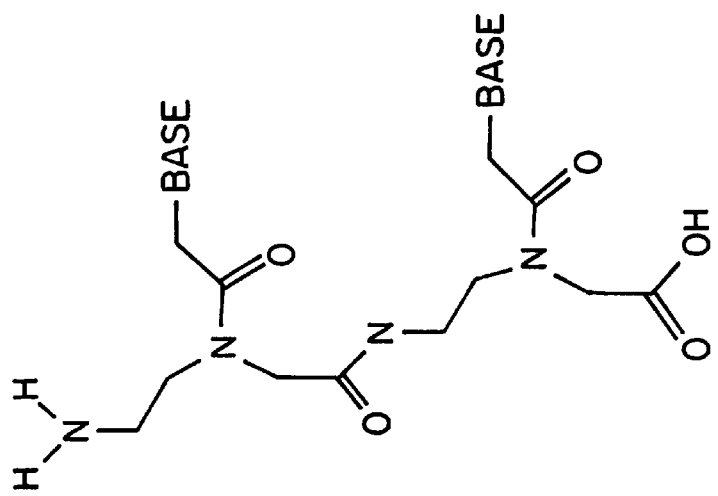
Figure 1A:
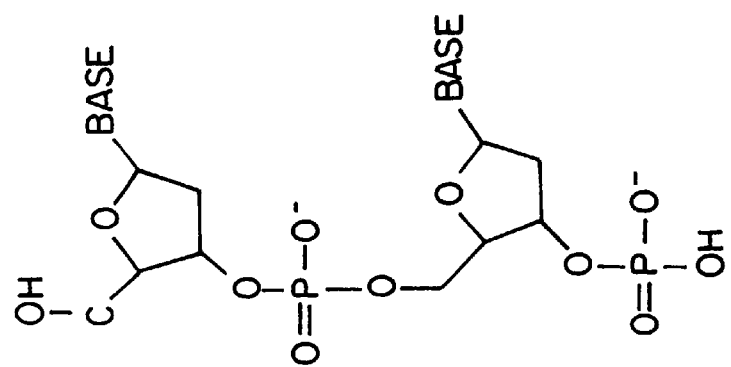
Figure 2A:
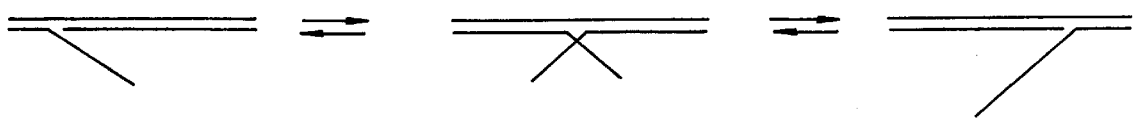
FIGS. 2A–C: Schematic description of purification of telomerase by use of capture PNA and release PNA species. (Panel A) Branch migration between two polynucleotides in solution equilibrium. (Panel B) Displacement of a strand of a double-stranded helix by strand invasion and total displacement by a release PNA forming a stable hybrid having greater thermodynamic stability. (Panel C) Scheme for capture and release of telomerase using PNA capture and release species and exemplified with a streptavidin-coated bead (B: biotin group; S: streptavidin linked to bead).
Figure 2B:
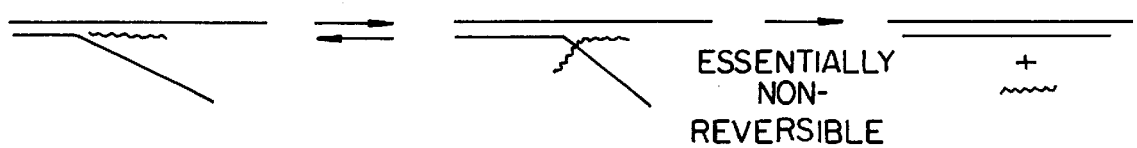
Figure 2C:
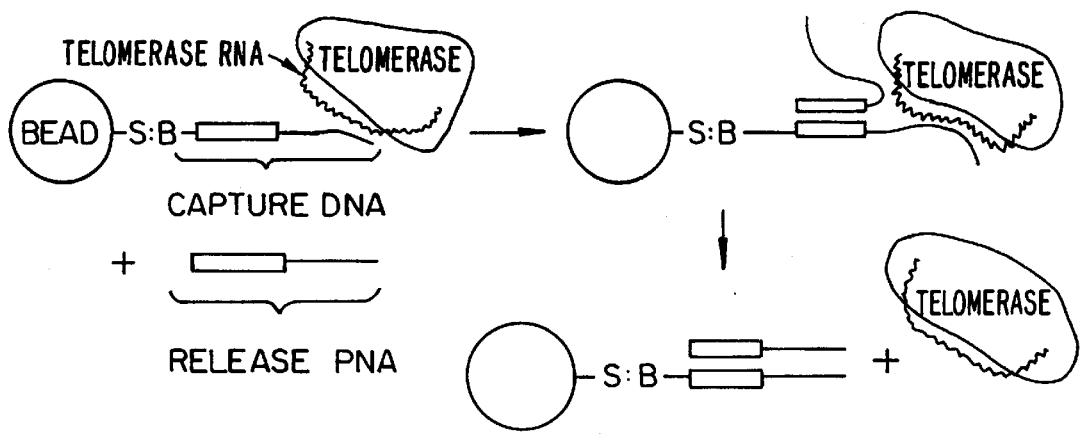

"Peptide nucleic acid," or "PNA" refers to a DNA analog in which the phosphate backbone has been replaced by (2-aminoethyl) glycine carboyl units that are linked to the nucleotide bases by the glycine amino nitrogen and methylene carbonyl linkers. The backbone is thus composed of peptide bonds linking the nucleobases (see FIG. 1). Because the PNA backbone is composed of peptide linkages, the PNA is typically referred to as having an amino-terminal and a carboxy-terminal end. However, a PNA can be also referred to as having a 5' and a 3' end in the conventional sense as described below, with reference to the complementary nucleic acid sequence to which it specifically hybridizes. The sequence of a PNA molecule is described in conventional fashion as having nucleotides G, U, T, A, and C that correspond to the nucleobase sequence of the PNA molecule.

Such polynucleotides can be synthesized, for example, using an automated DNA synthesizer. Typically, PNAs are synthesized using either Boc or Fmoc chemistry (see, e.g., Norton et al., *Bioorg. and Med. Chem* 3: 437–445 (1995)). PNAs and other polynucleotides can be chemically derivatized by methods known to those skilled in the art. For example, PNAs have amino and carboxy groups at the 5' and 3' ends, respectively, that can be further derivatized.

"Nucleic acid" typically refers to large polynucleotides. "Oligonucleotide or oligomer" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T" at some or all occurrences of T.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides.

Conventional notation is used herein to portray polypeptide sequences: the left-hand end of polypeptide sequences is the amino-terminus; the right-hand end of polypeptide sequences is the carboxyl-terminus.

"Enhanced cellular uptake" refers to the ability of a polypeptide sequence to increase the cell membrane permeability of PNAs. The phrase includes polypeptides that have the ability to "translocate" a RNA across a cell membrane, e.g., subsequences of homeodomain proteins and the h-region of a signal peptide.

"Corresponds to" means that a polynucleotide sequence is substantially identical to all or a portion of a reference polynucleotide sequence, or that a polypeptide sequence is identical to a reference polypeptide sequence. In contradistinction, the term "complementary to" means that the complementary sequence is substantially identical to all or a portion of a reference polynucleotide sequence. For illustration, the nucleotide sequence "5'-TATAC" corresponds to a reference sequence "5'-TATAC" and is complementary to a reference sequence "5'-GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison:, a reference sequence may be a subset of a larger sequence, for example, as a segment of a full-length telomerase RNA component gene sequence. Generally, a reference sequence is at least 20 nucleotides in length, frequently at least 25 nucleotides in length, and often at least 50 nucleotides in length. Since two polynucleotides may each comprise (1) a sequence (i.e., a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window" refers to a conceptual segment of at least 25 contiguous nucleotide positions wherein a polynucleotide sequence may be compared to a reference sequence of at least 25 contiguous nucleotides and wherein the portion of the polynucleotide sequence in the comparison window may comprise additions or deletions (i.e., gaps) of 20 percent or less as compared to the reference sequence (which for comparative purposes in this manner does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci.* (*U.S.A.*) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

"Sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The term "substantial identity" denotes a characteristic of a polynucleotide sequence, wherein the polynucleotide comprises a sequence that has at least 80 percent sequence identity, preferably at least 85 percent identity and often 89 to 95 percent sequence identity, more usually at least 99 percent sequence identity as compared to a reference sequence over a comparison window of at least 20 nucleotide positions, optionally over a window of at least 30–50 nucleotides, wherein the percentage of sequence identity is calculated by comparing the reference sequence to the polynucleotide sequence that may include deletions or additions which total 20 percent or less of the reference sequence over the window of comparison. The reference sequence may be a subset of a larger sequence, for example, as a segment of the full-length telomerase RNA component nucleotide sequence.

"Specific hybridization" is the formation, by hydrogen bonding or nucleotide bases, of hybrids between a probe polynucleotide (e.g., a polynucleotide of the invention and a specific target polynucleotide (e.g., a telomerase RNA component or genomic gene sequence), wherein the probe preferentially hybridizes to the specific target such that, for example, a single band corresponding to, e.g., one or more of the RNA species of the telomerase RNA component gene (or specifically cleaved or processed telomerase RNA component species) can be identified on a Northern blot of RNA prepared from a suitable source (e.g., a somatic cell expressing telomerase RNA component). Such hybrids may be completely or only partially base-paired. Polynucleotides of the invention which specifically hybridize to mammalian telomerase RNA component or human telomeric sequences may be prepared on the basis of the sequence data provided herein and available in the patent applications described herein and scientific and patent publications noted above, and according to methods and thermodynamic principles known in the art and described in Sambrook et al. et al., *Molecular Cloning: A Laboratory Manual*, 2nd Ed., (1989), Cold Spring Harbor, N.Y.; Berger and Kimmel, *Methods in Enzymology*, Volume 152, *Guide to Molecular Cloning Techniques* (1987), Academic Press, Inc., San Diego, Calif.; Goodspeed et al. (1989) *Gene* 76: 1; Dunn et al. (1989) *J. Biol. Chem.* 264: 13057, and Dunn et al. (1988) *J. Biol. Chem.* 263: 10878.

"Suitable binding conditions" refer to aqueous conditions wherein a mammalian telomerase RNA component associates with its cognate protein component and forms an enzymatically active telomerase holoenzyme capable of catalytic replication, repair, and/or addition of telomeric repeats from a suitable template, generally comprising telomeric repeats; such telomere repeat template may be present or absent. Often, suitable binding conditions can be physiological conditions. "Physiological conditions" refers to temperature, pH, ionic strength, viscosity, and like biochemical parameters that are compatible with a viable organism, and/or that typically exist intracellularly in a viable cultured mammalian cell, particularly conditions existing in the nucleus of said mammalian cell. For example, the intranuclear or cytoplasmic conditions in a mammalian cell grown under typical laboratory culture conditions are physiological conditions. Suitable in vitro reaction conditions for in vitro transcription cocktails are generally physiological conditions, and may be exemplified by a variety of art-known nuclear extracts. In general, in vitro physiological conditions can comprise 50–200 mM NaCl or KCl, pH 6.5–8.5, 20–45° C. and 0.001–10 mM divalent cation (e.g., $Mg^{++}$, $Ca^{++}$); preferably about 150 mM NaCl or KCl, pH 7.2–7.6, 5 mM divalent cation, and often include 0.01–1.0 percent nonspecific protein (e.g., BSA). A non-ionic detergent (Tween, NP-40, Triton X-100) can often be present, usually at about 0.001 to 2%, typically 0.05–0.2% (v/v). Particular aqueous conditions may be selected by the practitioner according to conventional methods. For general guidance, the following buffered aqueous conditions may be applicable: 10–250 mM NaCl, 5–50 mM Tris HCl, pH 5–8, with optional addition of divalent cation(s), metal chelators, nonionic detergents, membrane fractions, antifoam agents, and/or scintillants.

"Label" or "labeled" refer to incorporation of a detectable marker, e.g., a radiolabeled amino acid or a recoverable label (e.g. biotinyl moieties that can be recovered by avidin or streptavidin). Recoverable labels can include covalently linked polynucleotide sequences that can be recovered by hybridization to a complementary sequence polynucleotide or PNA; such recoverable sequences typically flank one or both sides of a nucleotide sequence that imparts the desired activity, i.e., inhibition of telomerase activity. Various methods of labeling PNAs and polynucleotides are known in the art and may be used. Examples of labels include, but are not limited to, the following: radioisotopes (e.g., $^3H$, $^{14}C$, $^{35}S$, $^{125}I$, $^{131}I$), fluorescent or phosphorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for antibodies, transcriptional activator polypeptide, metal binding domains, epitope tags). In some embodiments, labels are attached by spacer arms of various lengths, e.g., to reduce potential steric hindrance.

"Statistically significant" means a result (i.e., an assay readout) that generally is at least two standard deviations above or below the mean of at least three separate determinations of a control assay readout and/or that is statistically significant as determined by Student's t-test or other art-accepted measure of statistical significance.

"Antineoplastic agent" refers to agents that have the functional property of inhibiting the development or progression of a neoplasm in a human, and may also refer to the inhibition of metastasis or metastatic potential.

"Transcriptional modulation" refers to the capacity to either enhance transcription or inhibit transcription of a structural sequence linked in cis; such enhancement or inhibition may be contingent on the occurrence of a specific event, such as stimulation with an inducer and/or may only be manifest in certain cell types.

"Transcription regulatory region" refers to a DNA sequence comprising a functional promoter and any associated transcription elements (e.g., enhancer, CCAAT box, TATA box, SP1 site, etc.) that are essential for transcription of a polynucleotide sequence that is operably linked to the transcription regulatory region.

"Receptor-recognition protein" or "rrP" refers to a polypeptide which when bound, either directly or indirectly, to an exogenous polynucleotide or PNA, enhances the intracellular uptake of the exogenous polynucleotide or PNA into at least one predetermined cell type (e.g., hepatocytes). A receptor-recognition protein may include, but is not limited to, the following: a galactose-terminal (asialo-) glycoprotein capable of being internalized into hepatocytes via a hepatocyte asialoglycoprotein receptor, a transferrin polypeptide, and/or other naturally-occurring non-immunoglobulin ligands of cell surface receptors. A receptor-recognition protein may include non-peptide components, such as carbohydrate and/or lipid moieties, in covalent linkage to the polypeptide component(s). In some embodiments, a receptor-recognition protein may comprise multichain proteins and/or multimeric proteins. Various alternative receptor-recognition proteins will be apparent to those of skill in the art and are provided in the published literature.

"Pharmaceutical composition" refers to a composition suitable for pharmaceutical use in a mammal. A pharmaceutical composition comprises a pharmacologically effective amount of an active agent and a pharmaceutically acceptable carrier. "Pharmacologically effective amount" refers to that amount of an agent effective to produce the intended pharmacological result.

"Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/foil emulsion, and various types of wetting agents and/or adjuvants. Suitable pharmaceutical carriers and formulations are described in *Remington's Pharmaceutical*

*Sciences*, 19th Ed. (Mack Publishing Co., Easton, 1995). Preferred pharmaceutical carriers depend upon the intended mode of administration of the active agent.

Typical modes of administration include enteral (e.g., oral) or parenteral (e.g., subcutaneous, intramuscular, or intravenous intraperitoneal injection; or topical, transdermal, or transmucosal administration).

"Prognostic value" refers to an amount of the RNA component of telomerase detected in a given cancerous cell type that is consistent with a particular prognosis for the cancer. The amount (including a zero amount) of RNA component of telomerase detected in a sample is compared to the prognostic value for the cell such that the relative comparison of the values indicates the likely outcome of the cancer's progression.

"Diagnostic value" refers to a value that is determined for the RNA component of telomerase detected in a sample, which is then compared to a normal range of the RNA component of telomerase in a cell such that the relative comparison of the values provides a reference value for diagnosing cancer. Depending upon the method of detection, the diagnostic value may be a determination of the amount of the RNA component of telomerase in a sample, but it is not necessarily an amount. The diagnostic value may also be a relative value, such as a plus or a minus score, and also includes a value indicating the absence of the RNA component of telomerase in a sample.

C. Human Telomerase RNA Component

Mammalian telomerase includes an RNA component. The RNA component of telomerase from humans and from mice have been isolated and sequenced. See, e.g., Feng et al. (1995) *Science* 269:1236–41, U.S. Pat. No. 5,583,016 and Blasco et al. (1995) *Science* 269:1267–1270.

Human genomic DNA encoding hTR has been cloned, sequenced and placed on deposit. A lambda clone designated "28-1" contains an ~15 kb insert containing human telomerase RNA component gene sequences. Clone 28-1 was deposited with the American Type Culture Collection pursuant to the Budapest Treaty and granted accession number ATCC 75925. Plasmid pGRN33 contains an ~2.5 kb HindIII-SacI insert containing sequences from lambda clone 28-1 that contain the sequence of hTR. Plasmid pGRN33 was deposited with the American Type Culture Collection pursuant to the Budapest Treaty and granted accession number ATCC 75926. A PstI fragment of the ~2.4 kb SauIIIA1-HindIII fragment of clone 28-1 also contains the hTR sequence. The sequence of the PstI fragment is provided in SEQ ID NO:22, below. The nucleotides of hTR are indicated above the sequence indicated by stars and numbered 1 to 451. The template region is underlined.

```
                                         #
    1 CTGCAGAGGATAGAAAAAAG0CCCTCTGATACCTCAAGTTAGTTTCACCTTTAAAGAAGG
      GACGTCTCCTATCTTTTTTC7GGGAGACTATGGAGTTCAATCAAAGTGGAAATTTCTTCC
      -PST1-

61 TCGGAAGTAAAGACGCAAAGCCTTTCCCGGACGTGCGGAAGGGCAACGTCCTTCCTCATG
      AGCCTTCATTTCTGCGTTTCGGAAAGGGCCTGCACGCCTTCCCGTTGCAGGAAGGAGTAC

121 GCCGGAAATGGAACTTTAATTTCCCGTTCCCCCCAACCAGCCCGCCCGAGAGAGTGACTC
      CGGCCTTTACCTTGAAATTAAAGGGCAAGGGGGGTTGGTCGGGCGGGCTCTCTCACTGAG

181 TCACGAGAGCCGCGAGAGTCAGCTTGGCCAATCCGTGCGGTCGGCGGCCGCTCCCTTTAT
      AGTGCTCTCGGCGCTCTCAGTCGAACCGGTTAGGCACGCCAGCCGCCGGCGAGGGAAATA 1         10        20        30
                                       *********************************
  241 AAGCCGACTCGCCCGGCAGCGCACCGGGTTGCGGAGGGTGGGCCTGGGAGGGGTGGTGGC
      TTCGGCTGAGCGGGCCGTCGCGTGGCCCAACGCCTCCCACCCGGACCCTCCCCACCACCG 40        50        60        70        80        90
         ************************************************************
  301 CATTTTTTGTCTAACCCTAACTGAGAAGGGCGTAGGCGCCGTGCTTTTGCTCCCCGCGCG
      GTAAAAAACAGATTGGGATTGACTCTTCCCGCATCCGCGGCACGAAAACGAGGGGCGCGC 100       110       120       130       140       150
        ************************************************************
  361 CTGTTTTTCTCGCTGACTTTCAGCGGGCGGAAAAGCCTCGGCCTGCCGCCTTCCACCGTT
      GACAAAAAGAGCGACTGAAAGTCGCCCGCCTTTTCGGAGCCGGACGGCGGAAGGTGGCAA 160       170       180       190       200       210
        ************************************************************
  421 CATTCTAGAGCAAACAAAAAATGTCAGCTGCTGGCCCGTTCGCCCCTCCCGGGGACCTGC
      GTAAGATCTCGTTTGTTTTTTACAGTCGACGACCGGGCAAGCGGGGAGGGCCCCTGGACG

HTR
        220       230       240       250       260       270
        ************************************************************
  481 GGCGGGTCGCCTGCCCAGCCCCCGAACCCCGCCTGGAGGCCGCGGTCGGCCCGGGGCTTC
      CCGCCCAGCGGACGGGTCGGGGGCTTGGGGCGGACCTCCGGCGCCAGCCGGGCCCCGAAG 280       290       300       310       320       330
        ************************************************************
  541 TCCGGAGGCACCCACTGCCACCGCGAAGAGTTGGGCTCTGTCAGCCGCGGGTCTCTCGGG
      AGGCCTCCGTGGGTGACGGTGGCGCTTCTCAACCCGAGACAGTCGGCGCCCAGAGAGCCC
```

```
                     -continued
         340       350       360       370       380       390
         ****************************************************************
601 GGCGAGGGCGAGGTTCAGGCCTTTCAGGCCGCAGGAAGAGGAACGGAGCGAGTCCCCGCG
    CCGCTCCCGCTCCAAGTCCGGAAAGTCCGGCGTCCTTCTCCTTGCCTCGCTCAGGGGCGC 400       410       420       430       440       450
         ****************************************************************
661 CGCGGCGCGATTCCCTGAGCTGTGGGACGTGCACCCAGGACTCGGCTCACACATGCAGTT
    GCGCCGCGCTAAGGGACTCGACACCCTGCACGTGGGTCCTGAGCCGAGTGTGTACGTCAA 721 CGCTTTCCTGTTGGTGGGGGGAACGCCGATCGTGCGCATCCGTCACCCCTCGCCGGCAGT
    GCGAAAGGACAACCACCCCCCTTGCGGCTAGCACGCGTAGGCAGTGGGGAGCGGCCGTCA 781 GGGGGCTTGTGAACCCCCAAACCTGACTGACTGGGCCAGTGTGCTGCAAATTGGCAGGAG
    CCCCCGAACACTTGGGGGTTTGGACTGACTGACCCGGTCACACGACGTTTAACCGTCCTC 841 ACGTGAAGGCACCTCCAAAGTCGGCCAAAATGAATGGGCAGTGAGCCGGGGTTGCCTGGA
    TGCACTTCCGTGGAGGTTTCAGCCGGTTTTACTTACCCGTCACTCGGCCCCAACGGACCT 901 GCCGTTCCTGCGTGGGTTCTCCCGTCTTCCGCTTTTTGTTGCCTTTTATGGTTGTATTAC
    CGGCAAGGACGCACCCAAGAGGGCAGAAGGCGAAAAACAACGGAAAATACCAACATAATG 961 AACTTAGTTCCTGCTCTGCAG   (SEQ ID NO:22)   (# = "7" IS A OR T)
    TTGAATCAAGGACGAGACGTC
                 -PST1-
```

D. Antisense PNAs

The invention relates to peptide nucleic acid compounds that specifically hybridize to a polynucleotide sequence of the template region of the RNA component of mammalian telomerase and that have a polynucleotide sequence of six to twenty-five nucleotides. These compounds are highly effective at binding to the telomerase RNA component and at inhibiting telomerase activity. Specifically, peptide nucleic acids ("PNAs") having such complementary sequences are effective and selective inhibitory of telomerase activity and can be formulated and used for a variety of applications, including but not limited to commercial laboratory reagents which inhibit telomerase activity in a telomerase assay, cell sample, cell culture, or whole animal, as well as pharmaceutical uses in veterinary and human subjects, such as for treatment of telomerase-related diseases as described herein.

One especially useful type of polynucleotide of the invention is an antisense (or antigene) PNA that can be used in vivo or in vitro to inhibit the activity of human telomerase. Antisense PNAs comprise a specific sequence of from about 6 to 25 nucleotides, preferable from about 10 to about 25 nucleotides (i.e., large enough to form a stable duplex but small enough, depending on the mode of delivery, to administer in vivo, if desired) nucleotides complementary to a specific sequence of nucleotides in the RNA component of human telomerase, preferably in the template region and usually including repeat sequence of human telomerase.

In particular, a method called "PNA scanning" reveals nucleotide positions of the template region of telomerase that are important binding determinants for PNAs. For example, cytidines 50–52, cytidine 56, and uridine 57 are important binding determinants in the template region. PNAs that specifically hybridize to these nucleotide positions provide effective inhibition of telomerase. In addition, PNAs that are complementary to these binding determinants in the template region are such effective telomerase inhibitors that they can be used at low concentrations. PNAs that are complementary to these binding determinants can be shorter in length but still provide effective telomerase inhibition.

The mechanism of action of such molecules can involve binding of the RNA component either to prevent assembly of the functional ribonucleoprotein telomerase, to prevent the RNA component from serving as a template for telomeric DNA synthesis, to destabilize the telomerase RNA component and reduce its half-life, and/or to inhibit transcription of the telomerase RNA component gene, and other effects.

The antisense oligomers of the invention that serve to inhibit telomerase activity in vivo and/or in vitro include the PNA species specifically described herein and other similar analogs. These oligomers can also be used to purify telomerase and/or inhibit telomerase activity in human and other mammalian cells.

Additional embodiments directed to modulation of telomerase activity include methods that employ specific antisense PNA polynucleotide analogs complementary to all or part of the human telomerase RNA component (hTR) sequences, such as antisense PNA polymers to the human telomerase RNA component gene or its transcribed RNA, including truncated forms which may be associated with telomerase holoenzyme. Such complementary antisense PNA polymers may include nucleotide substitutions, additions, deletions, or transpositions, so long as specific binding to the relevant target sequence corresponding to telomerase RNA component or its gene is retained as a functional property of the polymer.

Complementary antisense PNA polymers include soluble PNA oligomers which can hybridize specifically to telomerase RNA component species and/or prevent transcription of the telomerase RNA component gene (Ching et al. (1989) *Proc. Nat. Acad. Sci. U.S.A.* 86: 10006; Broder et al. (1990) *Ann. Int. Med.* 113: 604; Loreau et al. (1990) *FEBS Letters* 274: 53; Holcenberg et al., WO 91/11535; WO 91/09865; WO 91/04753; WO 90/13641; and EP 386563). Certain antisense polymers of the invention therefore inhibit production of functional telomerase RNA component. Since telomerase RNA component expression (transcription rate and/or RNA stability) is associated with activation and enzymatic activity of telomerase holoenzyme, antisense polymers that prevent transcription of RNA corresponding to telomerase RNA component and/or the interaction of telomerase RNA component with the protein component of human telomerase and/or the interaction of telomerase RNA component to telomeric sequences can inhibit telomerase activity and/or alter a phenotype, such as immortalization or neoplastic transformation, of cells expressing telomerase activity, as compared to a phenotype observed in the absence of antisense polynucleotides.

Compositions containing a therapeutically effective dosage of telomerase RNA component antisense PNA polymers can be administered for treatment of diseases which require telomerase activity for cellular pathogenesis (e.g., neoplasia) or to inhibit gamete production or maintenance (i.e., as a contraceptive), if desired. Antisense PNA polymers of various lengths may be produced, although such antisense polymers typically comprise a sequence of about at least 6 consecutive nucleotides which are substantially complementary to a naturally-occurring telomerase RNA component polynucleotide sequence, and typically are perfectly complementary to a human telomerase RNA component template region sequence, often being complementary to the sequence of telomerase RNA component which is complementary to the telomere repeat sequence, or complementary to a portion of the telomerase RNA component which contacts the telomerase polypeptide subunit.

The antisense PNA polymers may comprise soluble species that are administered to the external milieu, either in the culture medium in vitro or in interstitial spaces and bodily fluids (e.g., blood, CSF) for application in vivo. Soluble antisense polymers present in the external milieu can gain access to the cytoplasm and inhibit specific RNA species. In some embodiments the antisense PNA polymers comprise non-PNA moieties, as amino acid moieties, methylphosphonate moieties, C-5 propenyl moieties, 2' fluororibose sugars, or the like (see Egholm et al. (1992) *J. Am. Chem. Soc.* 114: 1895; Wittung et al. (1994) *Nature* 368: 561; Egholm et al. (1993) *Nature* 365: 566; Hanvey et al. (1992) *Science* 258: 1481). For general methods relating to antisense polynucleotides, see *Antisense RNA and DNA* (1988), D. A. Melton, Ed., Cold Spring Harbor Laboratory, Cold Spring Harbor, N.Y.

In addition, antisense polynucleotides can comprise a derivatized substituent which is substantially non-interfering with respect to hybridization to the RNA component of a mammalian telomerase. Antisense polymers that have been modified with appended chemical substituents may be introduced into a metabolically active eukaryotic cell to hybridize with a telomerase RNA component of telomerase in the cell. Typically such antisense polymers are derivatized, and additional chemical substituents are attached, either during or after polymer synthesis, respectively, and are thus localized to a complementary sequence in the telomerase RNA component where they produce an alteration or chemical modification to a local RNA sequence and/or to the telomerase protein component.

Preferred attached chemical substituents include: europium (III) texaphyrin, cross-linking agents, psoralen, metal chelates (e.g., iron/EDTA chelate for iron catalyzed cleavage), topoisomerases, endonucleases, exonucleases, ligases, phosphodiesterases, photodynamic porphyrins, chemotherapeutic drugs (e.g., adriamycin, doxirubicin), intercalating agents, base-modification agents, immunoglobulin chains, and oligonucleotides. Iron/EDTA chelates are particularly preferred chemical substituents where local cleavage of a polynucleotide sequence is desired (Hertzberg et al. (1982) *J. Am. Chem. Soc.* 104: 313; Hertzberg and Dervan (1984) *Biochemistry* 23: 3934; Taylor et al. (1984) *Tetrahedron* 40: 457; Dervan, P B (1986) *Science* 232: 464). Preferred attachment chemistries include: direct linkage, e.g., via an appended reactive cysteine group (Corey and Schultz (1988) *Science* 238: 1401) and other direct linkage chemistries, although streptavidin/biotin and digoxigenin/anti-digoxigenin antibody linkage methods may also be used.

Methods for linking chemical substituents are provided in U.S. Pat. Nos. 5,135,720, 5,093,245, and 5,055,556. Other linkage chemistries may be used at the discretion of the practitioner. PNA polymers which correspond to all or a substantial portion of a mammalian telomerase RNA component (i.e., "sense" polymers) may also be derivatized and used to react with telomerase proteins and or the telomerase component gene or telomeric repeat sequences in the genome and produce adducts or other modification of the chemical environment at such regions of the genome.

E. Other Inhibitory PNAs

In addition to the antisense polynucleotides of the invention, one can construct PNA oligomers that will bind to duplex nucleic acid either in the folded RNA component or in the gene for the RNA component, forming a strand-invasion, strand-displacement D-loop, triple helix-containing or triplex nucleic acid to inhibit telomerase activity and/or transcription or processing of the hTR gene. Such oligomers of the invention are constructed using the base-pairing rules of triple helix formation and the nucleotide sequence of the RNA component (Cheng et al. (1988) *J. Biol. Chem.* 263: 15110; Ferrin and Camerini-Otero (1991) *Science* 354: 1494; Ramdas et al. (1989) *J. Biol. Chem.* 264: 17395; Strobel et al. (1991) *Science* 254: 1639; Hsieh et al. (1990) op.cit.; Rigas et al. (1986) *Proc. Natl. Acad. Sci.* (U.S.A.) 83: 9591).

Such polynucleotides can block telomerase activity in a number of ways, including by preventing transcription of the telomerase gene or by binding to a duplex region of the RNA component of telomerase in a manner that prevents the RNA component either from forming a functional ribonucleoprotein telomerase or from serving as a template for telomeric DNA synthesis. Typically, and depending on mode of action, the oligomers of the invention comprise a specific sequence of from about 6 to about 25 to 200 or more (i.e., large enough to form a stable triple helix but small enough, depending on the mode of delivery, to administer in vivo, if desired) nucleotides complementary (in this context, complementary means able to form a stable triple helix or to strand-invade or displace or form D-loop structures) to a specific sequence in the RNA component of telomerase or the gene for the RNA component of telomerase.

F. Sense PNAs

In addition to the antisense PNA oligomers of the invention, sense PNAs identical in sequence to at least a portion of the RNA component of human telomerase can also be used to inhibit or induce telomerase activity. Oligomers of the invention of this type are characterized in comprising either (1) less than the complete sequence of the RNA component needed to form a functional telomerase enzyme or (2) the complete sequence of the RNA component needed to form a functional telomerase enzyme as well as a substitution or insertion of one or more nucleotides that render the resulting RNA non-functional. The mechanism of action of such oligomers thus involves the assembly of a non-functional ribonucleoprotein telomerase or the prevention of assembly of a functional ribonucleoprotein telomerase, such as by competitive inhibition of binding of hTR RNA to telomerase holoenzyme. Sense oligomers of the invention of this type typically comprise a specific sequence of from about 5, 10, 20, 50, 100, 200, 400, or more nucleotides identical to a specific sequence of nucleotides in the RNA component of mammalian, preferably human, telomerase.

G. Enhancing Cellular Uptake of PNAs

An important factor in the use of antisense compounds such as antisense PNAs is the ability of such compounds to traverse the plasma membrane of a cell, or the membrane of an intra-cellular compartment such as the nucleus. Cellular membranes are composed of lipid-protein bi-layers that are freely permeable to small, nonionic lipophilic compounds and are inherently impermeable to natural metabolites and therapeutic or diagnostic agents.

However, proteins have been described that have the ability to translocate across a cell membrane. Typically such proteins have amphiphilic or hydrophobic subsequences that have the ability to act as membrane-translocating carriers. For example, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, *Current Opinion in Neurobiology* 6: 629–634 (1996)). Another subsequence, the h (hydrophobic) domain of signal peptides, was found to have similar cell membrane translocation characteristics (see, e.g., Lin et al., *J. Biol. Chem.* 270: 1 4255–14258 (1995)).

Such subsequences can be used to translocate PNAs across a cell membrane. PNAs can be conveniently derivatized with such sequences. For example, PNAs can be synthesized with a thiol group that allows covalent linkage with a cysteine residue of the translocation polypeptide sequence. Alternatively, because PNAs have a peptide linkage backbone, peptide bonds can be used to link the PNA to the translocation subsequence. Optionally, a linker can be used to link the PNA and the translocation sequence. Any suitable linker can be used, e.g., an peptide linker or any other suitable chemical linker.

Examples of peptide sequences which can be linked to a PNA of the invention, such as for facilitating uptake of PNA into cells, include, but are not limited to: an 11 animo acid peptide of the tat protein of HIV; a 20 residue peptide sequence which corresponds to amino acids 84–103 of the p16 protein (see Fahraeus et al. (1996) *Current Biology* 6: 84); the third helix of the 60-amino acid long homeodomain of Antennapedia (Derossi et al. (1994) *J. Biol. Chem.* 269: 10444); or the h region of a signal peptide such as the Kaposi fibroblast growth factor (K-FGF) h region (Lin et al. supra). Other suitable chemical moieties that provide enhanced cellular uptake may also be chemically linked to suitable PNAs.

The PNA is also introduced into a mammalian cell by a transfection method. In an embodiment, the transfection methods comprise: (1) forming a transfection complex consisting essentially of a PNA, and a lipid component consisting essentially of a neutral and/or cationic lipid, optionally including a quaternary ammonium detergent and/or a lipopolyamine, optionally including a polycation (poly lysine, polyarginine, and the like), optionally including a receptor-recognition molecule that binds to a predetermined cell surface receptor (e.g., asialoglycoprotein receptor), and (2) contacting cells with the transfection complex, which can be in vitro, ex vivo, or in vivo.

In embodiments where a receptor recognition protein is included in the transfection complex, cells expressing the predetermined cell surface receptor with a composition comprising the receptor-recognition transfection complex under physiological transfection conditions which permit uptake of the PNA into said cells.

Polynucleotides can be linked to either end of a telomerase-modulating PNA of the invention. Such polynucleotides can also enhance cellular uptake. In one variation, the charged backbone of the linked polynucleotide enhances binding to cationic lipids, and facilitates formation and/or stability or other desired property(ies) of PNA:lipid delivery complexes. PNA:lipid delivery complexes include but are not limited to: liposomes comprising PNA, immunoliposomes comprising PNA, cationic lipid:PNA aggregates, polylysine:lipid:PNA complexes, polyarginine:lipid:PNA complexes, receptor recognition protein (rrP):lipid:PNA complexes, receptor recognition protein (rrP):polylysine:lipid:PNA complexes, receptor recognition protein (rrP):polyarginine:lipid:PNA complexes and the like.

H. Detecting the RNA Component of Telomerase

The method of detecting the presence, absence or amount of the RNA component of telomerase in a sample involves two steps: (1) specifically hybridizing a PNA polynucleotide to the template region of the RNA component of telomerase, and (2) detecting the specific hybridization. Detection refers to determining the presence, absence, or amount of the RNA component of telomerase in a sample, and can include quantitation of the amount of RNA component of telomerase per cell in a sample.

For the first step of the method, the PNA used for specific hybridization is chosen to hybridize to the template region of the RNA component of telomerase. Such PNAs allow efficient detection of hTR in cell extracts and tissue samples, as described herein. Suitable PNA lengths are from 6–50 nucleotides, preferably from 10–40 nucleotides, and most preferably from 12–25 nucleotides. Specific hybridization conditions are selected by those skilled in the art, as discussed herein.

For the second step of the reaction, any suitable method of detecting specific hybridization of a PNA to the RNA component of telomerase may be used. Detectable moieties used to detect hybridization include, e.g., labeled probes and PNAs.

PNAs that include detectable moieties are synthesized by standard methods known to those skilled in the art (see Ausubel, et al., and Sambrook, et al., supra). The detectable moiety may be directly or indirectly detectable and associated with either a primer or a probe. Directly detectable moieties include, e.g., polynucleotides that incorporate radioactive nucleotides. Indirectly detectable moieties include, for example, polynucleotides that incorporate biotinylated nucleotides recognized by streptavadin, or a nucleotide sequence, which is the binding partner for a radioactively labeled complementary sequence.

The detectable moiety often generates a measurable signal, such as a radioactive, chromogenic, or fluorescent signal, that can be used to quantitate the amount of bound detectable moiety, for example, for determination of a diagnostic value or a prognostic value for the RNA component of telomerase in a sample. Quantitation of the signal is achieved by methods known to those skilled in the art, for example, scintillation counting, densitometry, or flow cytometry. Determination of such a diagnostic value or a prognostic value allows comparison with a value for hTR in a normal cell sample. Using this comparison, a diagnosis or prognosis regarding the patient's sample may be determined.

Methods of determining whether a sample contains the RNA component of telomerase, and the amount of the RNA component, are particularly useful for diagnosis of cancer and determining its prognosis. In the diagnostic and prognostic methods of the invention, the assay is conducted to determine whether the RNA component of mammalian telomerase is present, whether the diagnostic value of the sample is higher than the value in a normal range of cells, and how the amount of the RNA component of telomerase in a sample compares to a prognostic value. The cells used to determine the normal range of RNA component expression can be normal cells from the individual to be tested, or normal cells from other individuals not suffering from a disease condition. The determination of a diagnostic value of the RNA component of mammalian telomerase above normal range is indicative of the presence of immortal cells, such as certain types of cancer cells, and these values can be used to aid or make a diagnosis even when the cells would be classified as non-cancerous by pathology. Comparison of the amount of the RNA component of mammalian telomerase with a prognostic value for a given cancerous cell type allows staging of the cancer and determination of a prognosis. Thus, the methods of the present invention allows cancerous conditions to be detected with increased confidence and possibly at an earlier stage, before cells are detected as cancerous based on pathological characteristics.

The diagnostic and prognostic methods of the present invention can be employed with any cell or tissue type of any origin and can be used to detect an immortal or neoplastic cell, or tumor tissue, or cancer, of any origin, provided the cell expresses telomerase activity and therefore its RNA component. For patient samples (referring to a sample for hTR detection), the detection of immortal cells will typically be used to detect the presence of cancer cells of any of a wide variety of types, including solid tumors and leukemias. Types of cancer that may be detected include, for example, adenocarcinoma of the breast, prostate, and colon; all forms of bronchogenic carcinoma of the lung; leukemias such as mixed cell, T-cell chronic, lymphocytic acute, lymphocytic chronic, and myeloid; Hodgkin's disease; melanoma; hepatoma; neuroblastoma; and papilloma. Typically, in situ hybridization assays will be used for heterogenous or focal diseases such as breast and prostate cancer, while tube-based solution assays will be used for homogenous tumors such as neuroblastoma.

The diagnostic and prognostic methods can also be carried out in conjunction with other diagnostic or prognostic tests. In some instances, such combination tests can provide useful information regarding the progression of a disease, although the present methods of testing for hTR provide much useful information in this regard. When the present methods are used to detect the presence of cancer cells in patient's sample, the presence of hTR can be used to determine the stage of the disease, whether a particular tumor is likely to invade adjoining tissue or metastasize to a distant location, and whether a recurrence of the cancer is likely. Tests that may provide additional information include diagnostic tests for the estrogen receptor, progesterone receptor, DNA ploidy, fraction of cells in S-phase, nodal status, and presence of oncogene gene products.

Those of skill in the art will also recognize that a variety of patient samples can be used in the methods of the invention. For example, cell extracts, cultured cells, or tissue samples provide convenient samples for use with the methods of the invention. The methods of the invention can use samples either in solution or extracts, or samples such as tissue sections for in situ methods of detection. Samples can also be obtained from sources such as cells collected from bodily fluids and wastes, e.g., urine, sputum, and blood; washes, e.g., bladder and lung; and fine-needle biopsies, e.g., from prostate, breast, and thyroid; cellular materials; whole cells; tissue and cell extracts; RNA extracted from tissue and cells; and histological sections of tissue.

The diagnostic and prognostic methods of the invention are carried out using methods of detecting the presence, absence or amount of the RNA component of mammalian telomerase, as described herein. A suitable cell sample is contacted with a PNA that can specifically hybridize to the RNA component of mammalian telomerase, and then the hybridization is detected using any of the methods described above.

The present invention also provides for kits for performing the diagnostic and prognostic method of the invention. Such kits can be prepared from readily available materials and reagents. For example, such kits can comprise any one or more of the following materials: enzymes, reaction tubes, buffers, detergent, primers and probes that target hTR, control reagents, and instructions. A wide variety of kits and components can be prepared according to the present invention, depending upon the intended user of the kit and the particular needs of the user.

I. Assays for Therapeutics

In one embodiment, candidate therapeutic PNAs are identified by their ability to block the binding of a telomerase protein component to a telomerase RNA component and/or to inhibit telomerase activity in a suitable activity assay (e.g., TRAP assay; see WO 95/13381. Typically, a telomerase RNA component used in these methods comprises a naturally occurring mammalian telomerase RNA component sequence (e.g., a human RNA component), although mutant telomerase RNA component sequences are sometimes used if the mutant telomerase RNA component binds to the telomerase protein component under control assay conditions (e.g., physiological conditions).

PNA species which specifically inhibit human telomerase activity are candidate antineoplastic agents, which are formulated for administration to a patient having a neoplasm. Candidate antineoplastic agents are then tested further for antineoplastic activity in assays which are routinely used to predict suitability for use as human antineoplastic drugs. Examples of these assays include, but are not limited to: (1) ability of the candidate agent to inhibit the ability of anchorage-independent transformed cells to grow in soft agar, (2) ability to reduce tumorigenicity of transformed cells transplanted into nulnu mice, (3) ability to reverse morphological transformation of transformed cells, (4) ability to reduce growth of transplanted tumors in nulnu mice, (5) ability to inhibit formation of tumors or preneoplastic cells in animal models of spontaneous or chemically-induced carcinogenesis, and (6) ability to induce a more differentiated phenotype in transformed cells to which the agent is applied.

Assays for detecting the ability of PNA species to inhibit or augment the telomerase protein component:telomerase RNA component binding and/or enzymatic activity of telomerase provide for facile high-throughput screening of banks of PNA species having varying nucleotide sequences and terminal modifications and/or terminal appended amino or imino acid residues, wherein the screens identify telomerase antagonist PNA species or agonist PNA species. Such antagonists and agonists may modulate telomerase activity and thereby modulate telomere repair competence and replicative potential.

J. Therapeutic and Prophylactic Aspects

PNAs that hybridize to the template region of the RNA component of telomerase can be used to inhibit telomerase activity. Because telomerase is active only in tumor, germline, and certain stem cells, for example stem cells of the hematopoietic system, other normal cells are not affected by telomerase inhibition therapy using PNA polymers of the present invention. Steps can also be taken to avoid contact of the telomerase inhibitor with germline or stem cells, although this may not be essential. For instance, because germline cells express telomerase activity, inhibition of telomerase may negatively impact spermatogenesis and sperm viability, and telomerase inhibitors may be effective contraceptives or sterilization agents. This contraceptive effect may not be desired, however, by a patient receiving a telomerase inhibitor of the invention for treatment of cancer. In such cases, one can deliver a telomerase inhibitor of the invention in a manner that ensures the inhibitor will only be produced during the period of therapy, such that the negative impact on germline cells is only transient, or more localized administration can be used.

These methods can be carried out by delivering to a patient, more particularly to diseased cells, a functional PNA of the invention to the cell. For instance, the PNA polymer can be delivered in a liposome or other delivery enhancement formulation. In certain embodiments, the PNA comprises a moiety which enhances uptake into cells or subcellular compartments (e.g., nucleus); such moieties can include polypeptide sequences such as an 11 amino acid peptide of the tat protein of HIV and/or a 20 residue peptide sequence which corresponds to amino acids 84–103 of the p16 protein (see Fahraeus et al. (1996) *Current Biology* 6: 84) and/or a suitable portion of a 60-amino acid long homeodomain of Antennapedia (Derossi et al. (1994) *J. Biol. Chem.* 269: 10444), or the h region of a signal peptide (Lin et al., *J. Biol. Chem.* 270: 14255–14258 (1995)).

Sense and antisense PNAs that hybridize near the hTR promoter, typically within 100–1000 nucleotides, can be used to activate or inhibit telomerase activity in various human cells that otherwise lack detectable telomerase activity due to low levels of expression of the RNA component or a protein component of telomerase. If the telomerase RNA component is not sufficient to stimulate telomerase activity, then the PNA can be introduced along with genes expressing the protein components of telomerase to stimulate telomerase activity. Thus, the invention provides methods for treating a condition associated with the telomerase activity within a cell or group of cells by contacting the cell(s) with a therapeutically effective amount of a PNA that alters telomerase activity in that cell.

Cells that incorporate PNAs having the property of stimulating hTR gene expression by D-loop formation near the promoter of the telomerase RNA gene can exhibit an increase in telomerase activity and an associated extended replicative life span. Such therapy can be carried out ex vivo on cells for subsequent introduction into a host or can be carried out in vivo. The advantages of stabilizing or increasing telomere length by adding PNA ex vivo to normal diploid cells include: telomere stabilization can arrest cellular senescence and allow potentially unlimited proliferative capacity of the cells; and normal diploid cells with an extended life span can be cultured in vitro for drug testing, virus manufacture, transplantation, or other useful purposes. In particular, ex vivo amplified stem cells of various types can be used in cell therapy for particular diseases, as noted above. Telomere stabilization can also suppress cancer incidence in replicating cells by preventing telomeres from becoming critically short as cells near crisis.

Cells that can be treated with PNA species that activate hTR transcription by D-loop formation at the promoter include but are not limited to hematopoietic stem cells (AIDS and post-chemotherapy), vascular endothelial cells (cardiac and cerebral vascular disease), skin fibroblasts and basal skin keratinocytes (wound healing and burns), chondrocytes (arthritis), brain astrocytes and microglial cells (Alzheimer's Disease), osteoblasts (osteoporosis), retinal cells (eye diseases), and pancreatic islet cells (Type I diabetes).

Typically, the therapeutic methods of the invention involve the administration of an oligomer that functions to inhibit or stimulate telomerase activity under in vivo physiological conditions and is sufficiently stable under those conditions. As noted above, modified nucleic acids may be useful in imparting such stability, as well as for ensuring delivery of the PNA oligomer to the desired tissue, organ, or cell. Methods useful for delivery of oligonucleotides for therapeutic purposes are described in Inouye et al., U.S. Pat. No. 5,272,065.

In related aspects, the invention features pharmaceutical compositions including a therapeutically effective amount of a telomerase inhibitor PNA or telomerase activator PNA of the invention. Pharmaceutical compositions of telomerase inhibitors of the invention include a PNA species which comprises at least six contiguous nucleotides complementary to a hTR template region sequence, or combinations of such species and/or with other pharmaceuticals in a pharmaceutically acceptable carrier or salt. Other pharmaceutical compositions of the invention comprise a telomerase activator PNA preparation.

The therapeutic agent can be provided in a formulation suitable for parenteral, nasal, oral, or other mode of administration (see International patent application publication No. WO 93/23572, supra).

In another aspect of the invention, buffered aqueous solutions comprising at least one telomerase-inhibitory or activating PNA species of the invention at a concentration of at least 1 nM but not more than about 100 mM is formulated for administration, usually at a concentration of about 0.1 mM to 10 mM, typically by intravenous route, to a patient undergoing antineoplastic chemotherapy. The buffered aqueous solutions of the invention may also be used, typically in conjunction with other established methods, for organ culture, cell culture, delivery to transformed cells, and ex vivo cellular therapies. Nonaqueous formulations, such as lipid-based formulations are also provided, including stabilized emulsions. The telomerase-modulating PNA compositions are administered by various routes, including intravenous injection, intramuscular injection, subdermal injection, intrapericardial injection, surgical irrigation, topical application, ophthalmologic application, lavage, gavage, enema, intraperitoneal infusion, mist inhalation, oral rinse, and other routes, depending upon the specific medical or veterinary use intended.

Administration of an efficacious dose of an PNA capable of specifically inhibiting telomerase activity to a patient can be used as a therapeutic or prophylactic method for treating pathological conditions (e.g., cancer, inflammation, lymphoproliferative diseases, autoimmune disease, neurodegenerative diseases, and the like), which are effectively treated by modulating telomerase activity and DNA repair and replication.

The telomerase-modulating PNA species of the present invention can be administered as a pharmaceutical composition comprising the compound in combination with a pharmaceutically acceptable excipient. Such excipients include water, saline, Ringer's solution, dextrose solution, and solutions of ethanol, glucose, sucrose, dextran, mannose, mannitol, sorbitol, polyethylene glycol, phosphate, acetate, gelatin, collagen, and the like. One may additionally include other suitable preservatives, stabilizers and antimicrobials, antioxidants, buffering agents and the like. Typically, a PNA of the invention is formed in a pharmaceutical dosage form comprising an excipient and not less than 1 μg nor more than about 100 grams of at least one telomerase-modulating PNA species of the invention. In another aspect of the invention, buffered aqueous solutions comprising at least one telomerase-modulating PNA species of the invention at a concentration of at least 1 nM but generally not more than about 100 mM is formulated for administration, usually at a concentration of about 0.1 μM to 10 mM, typically by intravenous route or via in infusion pump for localized delivery (e.g., to a solid tumor) or sustained dosing.

Alternatively, one may incorporate or encapsulate the telomerase-modulating PNAs in a suitable polymer matrix, liposome or membrane, thus providing a sustained release delivery device suitable for implantation near the site to be treated locally. In general, with sustained release delivery, the formulations are constructed so as to achieve a constant concentration which will be bioequivalent to about 100 times the serum level of PNA of 10 times the tissue concentration. Nonaqueous formulations, such as lipid-based formulations are also provided, including stabilized emulsions. The telomerase-modulating PNA compositions are administered by various routes, including intravenous injection, intramuscular injection, subdermal injection, intrapericardial injection, surgical irrigation, topical application, ophthalmologic application, lavage, gavage, enema, intraperitoneal infusion, mist inhalation, oral rinse, and other routes, depending upon the specific medical or veterinary use intended.

The amount of telomerase-modulating PNA required to treat any particular disorder will of course vary depending on the nature and severity of the disorder, the age and condition of the patient, and other factors readily determined by one of skill in the art. Suitable dosages are from 1 ng/kg to about 1000 mg/kg, more preferably 1 μg/kg to about 100 mg/kg.

As will be apparent to those of skill in the art upon reading of this disclosure, the present invention provides valuable reagents relating to human telomerase, as well as a variety of useful therapeutic and diagnostic methods. The above description of necessity provides a limited sample of such methods, which should not be construed as limiting the scope of the invention. Other features and advantages of the invention will be apparent from the following examples and claims.

The above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

The following examples describe specific aspects of the invention to illustrate the invention and provide a description of the compounds and methods of the invention. The examples should not be construed as limiting the invention, as the examples merely provide specific methodology useful in understanding and practice of the invention.

EXAMPLES

The abbreviations used are: RNA-P, RNA polymerase; PS, phosphorothioate; PNA, peptide nucleic acid; hTR, the RNA component of human telomerase; TRAP; Telomeric repeat amplification protocol; TS primer, oligonucleotide primer that can be extended by telomerase; $IC_{50}$, Concentration of inhibitor required to eliminate 50% of enzymatic activity; ITAS, internal amplification standard; AEBSF, 4-(2aminoethyl)benzenesulfonyl fluoride; PCR, polymerase chain reaction.

Example 1
Inhibition of Telomerase Activity with PNAs
1. Introduction

PNAs were shown to recognize the RNA component of human telomerase (hTR) and inhibit activity of the enzyme within cell extracts or whole cells in picomolar to nanomolar concentrations. Inhibition of telomerase activity by PNAs is specific and potent and depends on targeting of exact functional boundaries of hTR template region. Inhibition by PNAs is 10–50 fold more efficient than the analogous phosphorothioate (PS) oligomers. In contrast to high selectivity of inhibition by PNAs, PS oligomers also inhibit telomerase in a nonsequence-selective fashion. These results demonstrate that the specificity and high affinity of PNA recognition can be employed to control the enzymatic activity of ribonucleoproteins, and that PNAs possess important advantages relative to PS oligomers in both the affinity and the specificity of their recognition. These observations provide effective inhibitors of telomerase activity and affinity probes of telomerase structure.

The results of the demonstrations hereinbelow show that PNAs can inhibit telomerase efficiently and at low concentrations. PNAs inhibit telomerase activity when present at lower concentrations than analogous (sequence identical) phosphorothioate (PS). PS oligomers nonselectively inhibit telomerase. These results show that PNAs possess distinct advantages relative to PS oligomers and can be developed as inhibitors of ribonucleoproteins.

2. Materials and Methods
a. Preparation of PNA and PS Oligomers

PNA monomers were obtained from PerSeptive Biosystems. Anhydrous dimethyl formamide was purchased from Aldrich. Peptide monomers and derivatized resin were obtained from Peptides International. PNAs were synthesized manually following t-boc peptide chemistry as described (Norton et al. (1995) *Bioorganic and Medicinal Chemistry* 3: 437) with the following modifications. The syntheses for PNAs I-VIII, IX and X, and XI-XIII were accomplished simultaneously. These PNAs possess the same sequence at their carboxy termini. Synthesis was carried out from carboxy to amino terminus and, as a desired PNA length was reached, a fraction of total resin was removed. The removed resin was capped with glycine to complete the desired polymer chain. Following complete synthesis the product was cleaved off the resin and deprotected by treatment with trifluormethanesulfonic acid:trifluoroacetic acid:m-cresol:thioanisole (2:6:1:1) for 1 hour. The product was precipitated with diethylether and collected. Following purification by reverse phase HPLC as described (Norton et al. (1995) op.cit) the identity of each PNA was confirmed by mass spectroscopy. PS oligonucleotides were synthesized using reagents obtained from Applied Biosystems. PS and phosphodiester oligonucleotides were synthesized using an Applied Biosystems 451 DNA synthesizer.

b. Preparation of Cell Extracts and Permeabilized Cells

Cells were derived from a human immortal primary breast epithelial cell line (HME50-5) that expresses telomerase at high levels. Cell extracts were obtained by resuspending a 100,000 cell pellet into 200 μl of lysis buffer (0.5% 3-[3-cholamidopropyl-dimethylammonio]-1-propane-sulfonate (CHAPS), 10 mM Tris-HCl, pH 7.5, 1 mM ethylenebis (oxyethylene-nitrilo)tetraacetic acid (EGTA), 5 mM β-mercaptoethanol, 0.1 mM 4-(2-aminoethyl) benzenesulfonyl fluoride (AEBSF), 10% glycerol). The suspension was mixed by pipetting at least three times and kept on ice for 30 minutes. The lysate was centrifuged at 16,000×g for 20 minutes at 4° C., and 160 μl of the supernatant was collected. The cells were then diluted 10-fold to obtain a 50 cell equivalent/μl stock suspension, aliquoted, frozen in liquid nitrogen, and stored at −80° C. These aliquots were utilized throughout our experiments to ensure consistency.

To examine the ability of PNAs to inhibit telomerase activity within permeabilized cells HME50-5 cells were treated with a buffered solution containing a relatively low concentration of detergent (20 mM Tris-HCl, pH 8.3, 1.5 mM $MgCl_2$, 68 mM KCl, 0.5% Tween 20, 1 mM EGTA, 5.0% glycerol, and 0.1 mM AEBSF). The telomerase activity in these cells was not further purified, and permeabilized cells were incubated with PNA and PS oligomers prior to assay for telomerase activity.

A further control experiment was performed to ensure that the observed. inhibition was due to PNA entry into permeabilized cells The TRAP assay was utilized to compare the level of telomerase activity retained inside permeabilized cells to activity which leaks into solution. This control was necessary to ensure that the observed inhibition was due to PNA inhibition of telomerase within cells. Permeabilized cells were centrifuged and the cell pellet and the cell-free supernatant were separately examined for telomere activity using the TRAP assay. Greater than 80% of telomerase activity remained associated with the cell pellet after this mild treatment, confirming that telomerase is largely retained inside permeabilized cells.

c. Measurement of Telomerase Activity

Telomerase activity was determined using the telomere repeat amplification protocol (TRAP) assay essentially as described (Piatyszek et al. (1995) *Methods in Cell Science* 17: 1) with the modification that the cellular extract was preincubated at 25° C. for 30 minutes with the PNA at the concentrations indicated. Following preincubation 3 μl of the cellular extract plus PNA was added to a PCR tube containing 46 μl of reaction buffer (20 mM Tris-HCl, pH 8.3, 1.5 MM $MgCl_2$, 68 MM KCl, 0.05% Tween-20, 1 mM EGTA), 50 μM dNTPs, 0.1 μg TS primer (5'-AATCCGTCGAGCAGAGTT-3' (SEQ ID NO:23)), 5 attg ITAS template (25), 0.5 μM T4 gene 32 protein, 2 Units Taq polymerase, 4 μ$Ci^{32}$P-α dCTP) above a wax barrier separating 0.1 μg of the CX, reverse primer (5'-CCCTTACCCTTACCCTTACCCTAA-3' (SEQ ID NO:24)), and incubated for 30 minutes to allow telomerase to elongate the TS primer. The tubes were transferred to a PCR thermocycler set at 94° C. for 3 minutes to melt the wax barrier, cycled 30 times (30 seconds at 95° C., 30 seconds at 55° C. and 30 seconds at 72° C.) followed by a 3 minute extension at 72° C. The samples were frozen at −80° C. and the wax barrier removed. The solution containing the PCR products (40 μl) was added to 3.3 μl of loading buffer and 20 μl was loaded onto a 10% non-denaturing polyacrylamide gel and separated by electrophoresis at 180 volts for 45 minutes followed by 280 volts for 1 hour and 45 minutes. Gels were fixed for 30 minutes (1:1 ethanol: water, 0.5 M NaCl, 40 mM NaOAc, pH 4.2) then exposed to a phosphorimager screen for quantitation. Phosphorimager analysis was performed utilizing a Molecular Dynamics model 425F phosphorimager. Data was processed using ImageQuant software version 3.3.

d. Estimation of $IC_{50}$ Values or Inhibition of Telomerase Activity

Varied concentrations of PNA were added to cell extracts containing the TS primer. Telomerase products were visualized by gel electrophoresis and the extent of inhibition was quantified by phosphorimager analysis by evaluating each lane of the gels separately. The lanes were further separated into two areas for evaluation; one for the internal amplification standard (ITAS) and the other for all telomerase products. A ratio of telomerase products to ITAS was determined and compared to a positive control in which no PNA had been added. This ratio was taken to indicate telomerase activity with the ratio of the positive control being assigned 100% activity. The extent of inhibition as a function of the concentration of the added PNA was plotted and these graphs were utilized to derive the $IC_{50}$.

e. Measurement of $K_{m\ app}$ for TS Primer

Telomerase assays were performed essentially as described above with slight modifications. Both the TS and CX primers (0.1 μg) were placed below the wax barrier and the concentration of TS primer was varied from 0 nM to 60 nM, above the wax barrier, in the reaction mixture. The reaction was allowed to proceed for 30 minutes at 25° C. followed by PCR as described. The products were quantitated as described with telomerase activity relative to control plotted versus the TS primer concentration. The TS primer concentration at which 50% of maximal telomerase activity was achieved was taken to be a $K_{m\ app}$ of telomerase for the TS primer.

3. Results a. TRAP Assay as a Measure of Telomerase Activity

Telomerase activity was measured using the telomeric repeat amplification protocol (TRAP). Rather than measure the change in chromosome length over time, a process that requires weeks to produce definitive results and measures telomerase activity only indirectly, the TRAP assay measures the elongation of a short oligonucleotide primer (TS primer) known to act as an efficient substrate of telomerase. Cell extracts from a human immortal breast epithelial cell line, HME50-5, expressing telomerase were preincubated with PNAs to allow recognition of complementary sequences by Watson-Crick base-pairing. The TS primer was then added to initiate chain elongation by telomerase. Following elongation of the TS primer, the mixture was transferred to a thermocycler and polymerase chain reaction (PCR) was performed to amplify the products. Two potential template DNAs were present, and amplification products were primed from either an internal amplification standard (ITAS) or from the product of telomerase elongation of the TS primer. These amplification products were separated by gel electrophoresis and quantitated separately. A ratio of the amount of amplified products of telomerase activity to that derived from amplification of the ITAS standard was determined and compared to a positive control to which no PNA was added. This comparison allowed calculation of the inhibition of telomerase activity due to a given concentration of PNA.

b. Inhibition of Telomerase Activity in Purified Extracts by PNAs

Figure 3A:
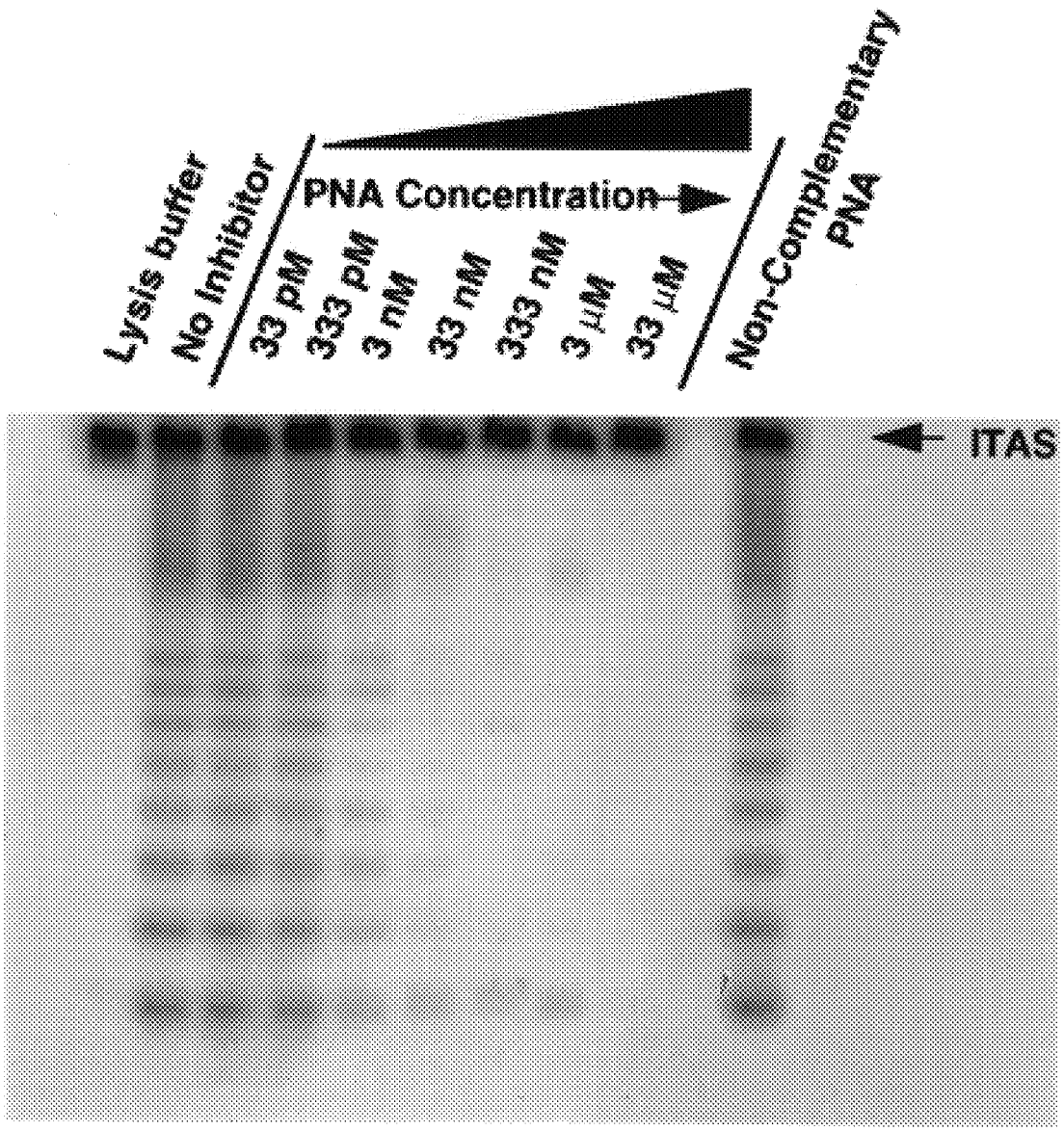
FIGS. 3A–B: (Panel A) TRAP assay results (products of reaction after gel electrophoresis) showing inhibition of telomerase activity by PNA XII; the location of the internal amplification standard (ITAS) is noted. (Panel B) Results of inhibition of telomerase activity in TRAP assay of Panel A graphed as a function of the concentration of PNA XII.
Figure 3B:
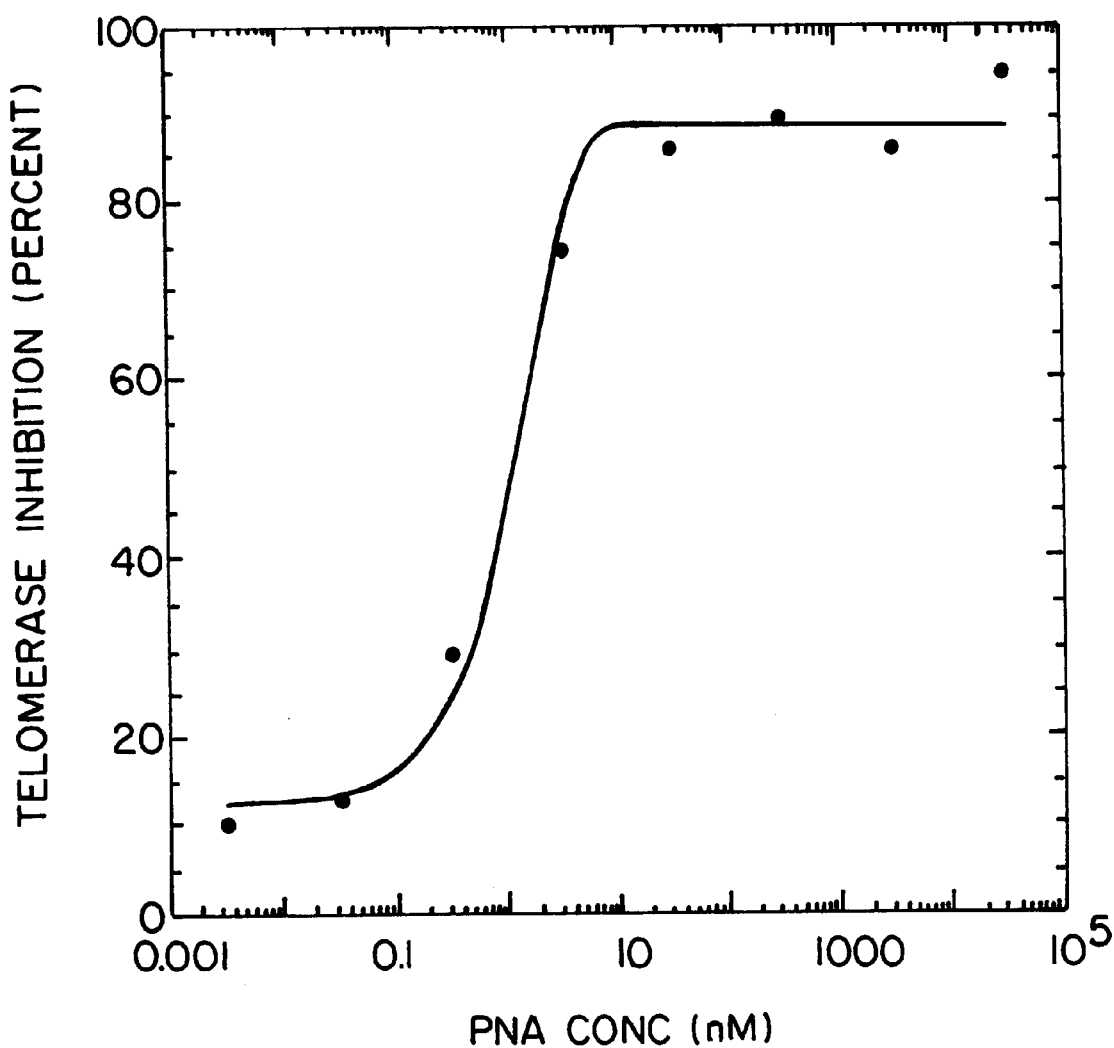

PNA oligomers of varied lengths were evaluated for their ability to inhibit telomerase activity (Table 1). PNAs were incubated with the crude extracts containing telomerase for thirty minutes to allow recognition of telomerase, after which the TS primer was added to initiate elongation. PNAs I, II, III, and IV were targeted to the 11 base template sequence and were shown to inhibit telomerase (Table 1). Inhibition increased with the length of PNA, as the 6, 9, 10, and 11 base PNAs possessed $IC_{50}$ values of 30, 1, 0.2, and 0.01 μM respectively. Addition of PNAs did not inhibit amplification of the control ITAS template, demonstrating that PNAs do not inhibit Taq polymerase or prevent hybridization of the amplification primers. Longer PNAs V–VIII which covered both the template and 3' distal regions of the RNA component of telomerase did not yield increased inhibition of telomerase. Indeed, the longest PNA, VIII, which was twenty nucleotides long, inhibited telomerase with an $IC_{50}$ value of 200 nM. Presumably, additional bases of the longer PNA offer more potential for nonspecific contacts in the extract or yield stronger intramolecular secondary structure, thereby reducing the likelihood of binding the telomerase target. Extension of PNAs to cover both the template and the 5' proximal region, PNAs IX, X, XI, XII, and XIII inhibited telomerase activity at $IC_{50}$ values in the range of 10 nM, with one exception, PNA XII, the best inhibitor to be identified in these studies, which possessed an $IC_{50}$ value of 0.9 nM (Table 1, FIG. 3). PNAs XIV and XV, which lacked complementarity to hTR, did not detectably inhibit human telomerase activity (Table 1). PNAs continued to inhibit telomerase activity with $IC_{50}$ values only slightly higher than those determined for inhibition within purified extracts at 37° C. Table 1 shows the nucleotide sequences of the respective PNA and PS polymers.

incubations of inhibited telomerase with primer and nucleotides under optimal conditions failed to generate elongated products.

d. Binding of TS Primer to Telomerase

Figure 5:
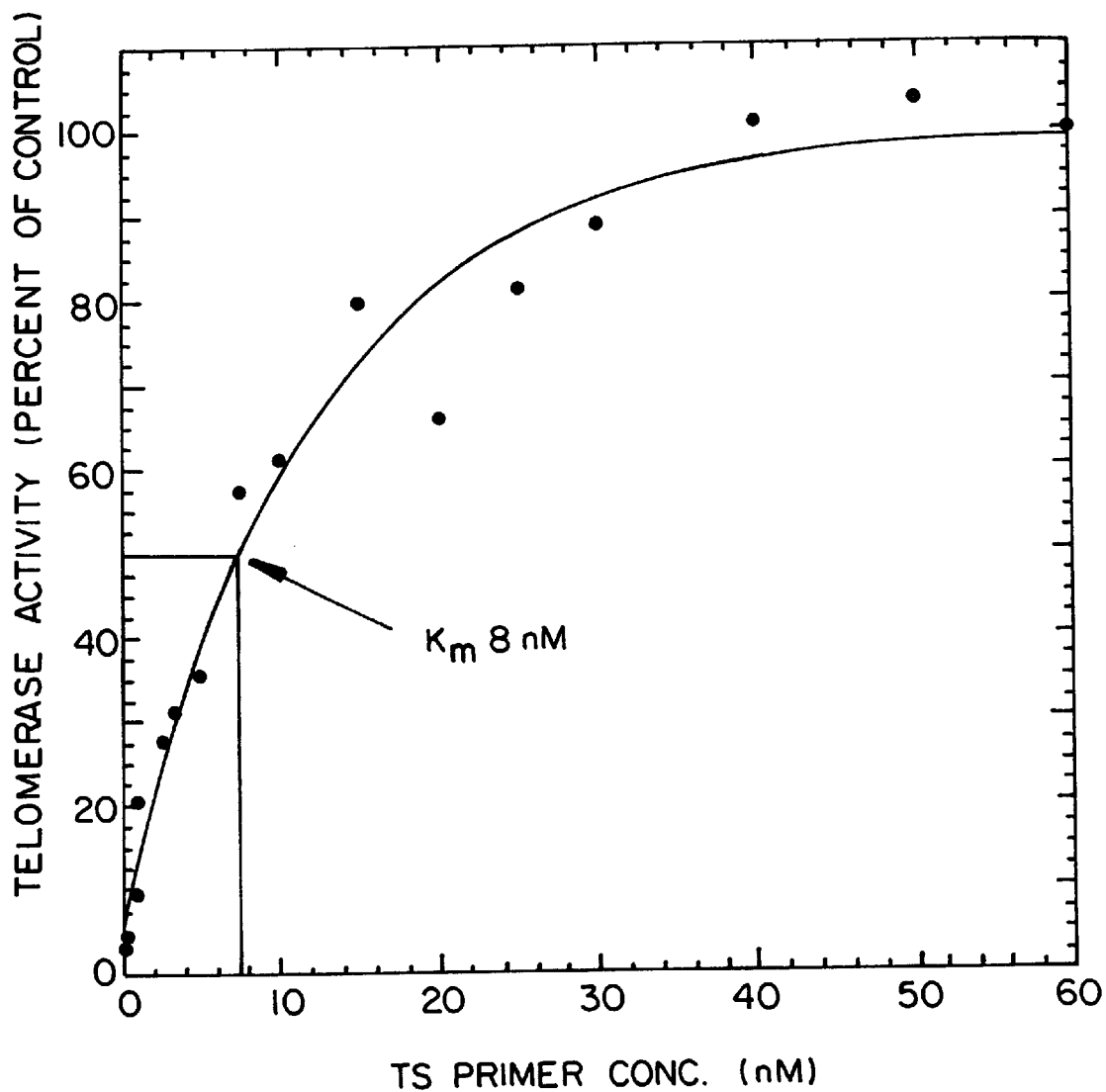
FIG. 5: Determination of Km (apparent) of telomerase for the TS primer. Telomerase assays and quantitations were performed essentially as described, infra. The concentration of TS primer was varied from 0 to 60 nM in the reaction mixture. The reaction was allowed to proceed for 30 minutes at 25° C. followed by amplification as described below. The products were quantitated as described with telomerase activity plotted as a function of the concentration of TS primer.

To put the efficiency of inhibition into context, the affinity of the TS primer for telomerase was determined. Primer affinity of telomerase was determined by monitoring the level of telomerase activity as a function of concentration of the TS primer. The TS primer is complementary to only three bases of the RNA template of the hTR, and was not initially expected to bind tightly to telomerase. The TRAP assay was performed as described, except that the concentration of the TS primer above the wax barrier was varied from 0 to 60 nM. The concentration of TS primer below the wax barrier was varied to keep the total concentration constant. Surprisingly, however, we observed an apparent binding constant, $K_{m\ app}$, of 8 nM (FIG. 5). The high affinity suggests that interactions between telomerase and DNA primers are not limited to basepairing, and that there are additional interactions involving either the phosphate backbone or unpaired nucleotide bases of the primer.

e. Inhibition of Telomerase Activity in Permeabilized Cells

Relative to DNA, PNAs possess hydrophobic backbones which may increase interactions with hydrophobic proteins or membranes and non-sequence selective association with

TABLE 1

$IC_{50}$ Values for the inhibition of telomerase activity by PNA and PS oligomers.

| | Sequence | Cell Extract 25° C. | $IC_{50}$ (nM) 37° C. | Perm. Cells 37° C. | SEQ ID NO: |
|---|---|---|---|---|---|
| RNA STRAND | 3'-GGGAAGAGUCAAUCCCAAUCUGUUU-5' | | | | 40 |
| | Complementary PNA Sequence | | | | |
| PNA (I) | COOH-GGTTAG-NH$_2$ | 30,000 | | | — |
| PNA (II) | TAGGGTTAG | 1,000 | | | 6 |
| PNA (III) | TTAGGGTTAG | 200 | 400 | 500 | 7 |
| PNA (IV) | GTTAGGGTTAG | 10 | 100 | 300 | 13 |
| PNA (V) | AGTTAGGGTTAG | 10 | 75 | 370 | 8 |
| PNA (VI) | CAGTTAGGGTTAG | 10 | 50 | 75 | 4 |
| PNA (VII) | CTCAGTTAGGGTTAG | 10 | 70 | 100 | 2 |
| PNA (VIII) | CCCTTCTCAGTTAGGGTTAG | 200 | 300 | 400 | 4 |
| PNA (IX) | TAGGGTTAGAC | 10 | | | 10 |
| PNA (X) | GTTAGGGTTAGAC | 10 | | | 12 |
| PNA (XI) | GGGTTAGACAA | 10 | 50 | 70 | 3 |
| PNA (XII) | TAGGGTTAGACAA | 0.9 | 5 | 50 | 4 |
| PNA (XIII) | GTTAGGGTTAGACAA | 10 | 50 | 100 | 5 |
| | Non-Complementary PNA Sequence | | | | |
| PNA (XIV) | AGGATCTTCACCTAGATCCT | N/D | N/D | | 42 |
| PNA (XV) | TGTAAGGAACTAG | N/D | N/D | | 43 |
| | Complementary PS Sequence | | | | |
| PS (I) | 5'-GTTAGGGTTAG-3' | 75 | 250 | | 44 |
| PS (II) | CTCAGTTAGGGTTAG | 100 | 700 | | 45 |
| PS (III) | TAGGGTTAGACAA | 50 | 200 | | 46 |
| | Non-Complementary PS Sequence | | | | |
| PS (IV) | AGGATCTTCACCTAGATCCT | 100 | 400 | | 47 |
| PS (V) | TGTAAGGAACTAG | 100 | 450 | | 48 |

N/D; no inhibition detected at 33 μM PNA concentration.

c. Inhibition of Telomerase as a Function of PNA Concentration and Time

Figure 4:
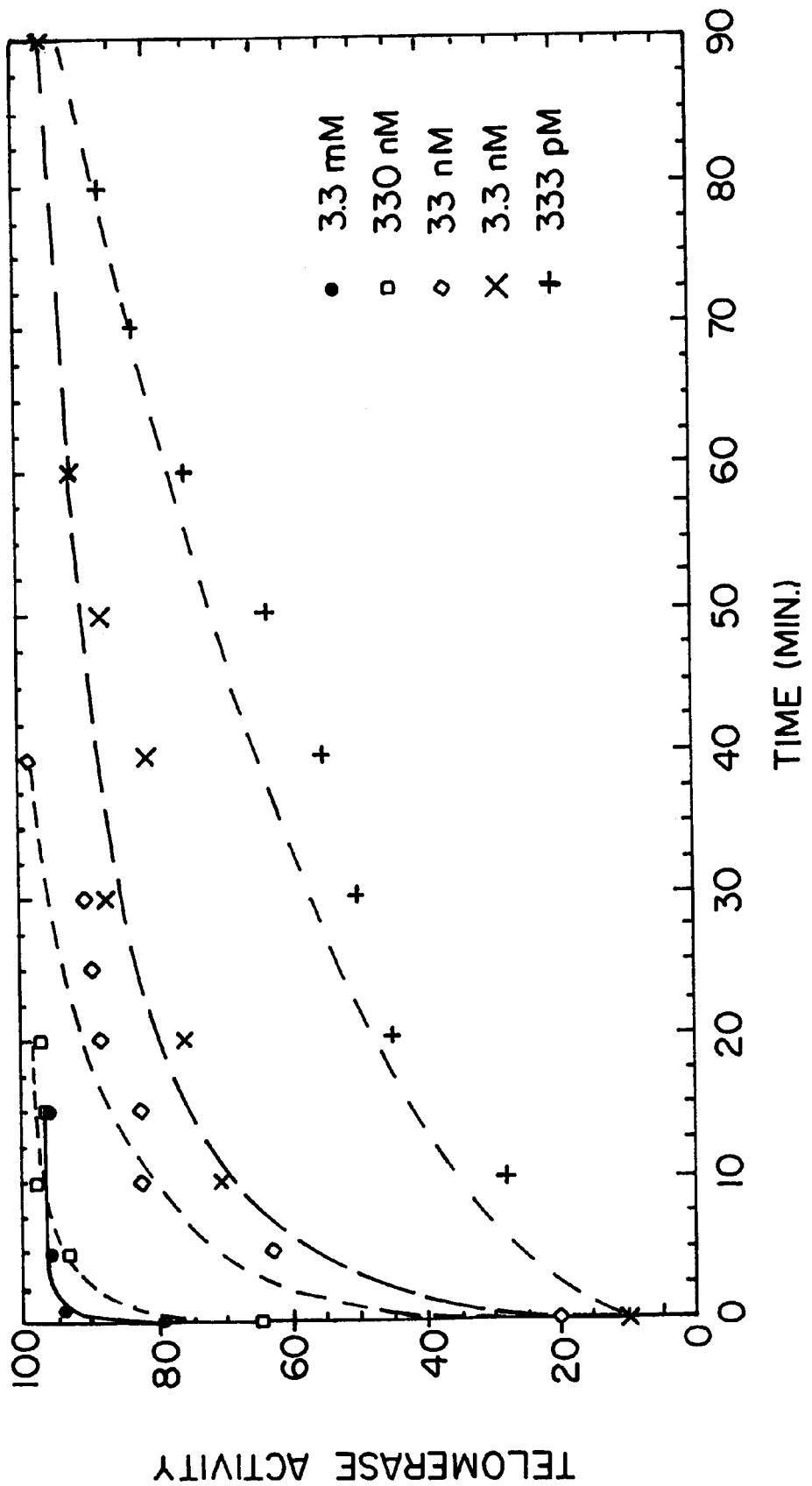
FIG. 4: Inhibition of telomerase as a function of PNA XII concentration and the time allowed for incubation of the PNA with telomerase.

Inhibition was dependent on the concentration of PNA and the time allowed for preincubation with cell extracts containing telomerase (FIG. 4). The presence of 200 nM PNA XII allowed maximal inhibition to be reached after a five minute preincubation of PNA and telomerase. A 300 pM concentration of PNA XII, by contrast, required ninety minutes to achieve maximal inhibition. Once maximal inhibition was attained, it was effectively irreversible. Lengthy RNA or chromosomal DNA. The potential for such interactions to interfere with the location of hTR by PNAs was evaluated by examining elongation under conditions more similar to those in vivo. PNAs were applied to HME50-5 cells that had been mildly permeabilized. Permeabilization facilitates PNA entry into cells, while the retention of telomerase inside cells requires that successful targeting of the RNA template of hTR occur in spite of the high concentrations of endogenous macromolecules. Incubations were performed at 37° C. to further mimic physiologic conditions. Greater than eighty percent of telomerase activity was determined to reside within cells after permeabilization. PNAs continued to inhibit telomerase activity with $IC_{50}$ values only slightly higher than those determined for inhibition within purified extracts at 37° C. (Table 1).

f. Inhibition of Telomerase Activity by PS Oligonucleotides

Figure 6:
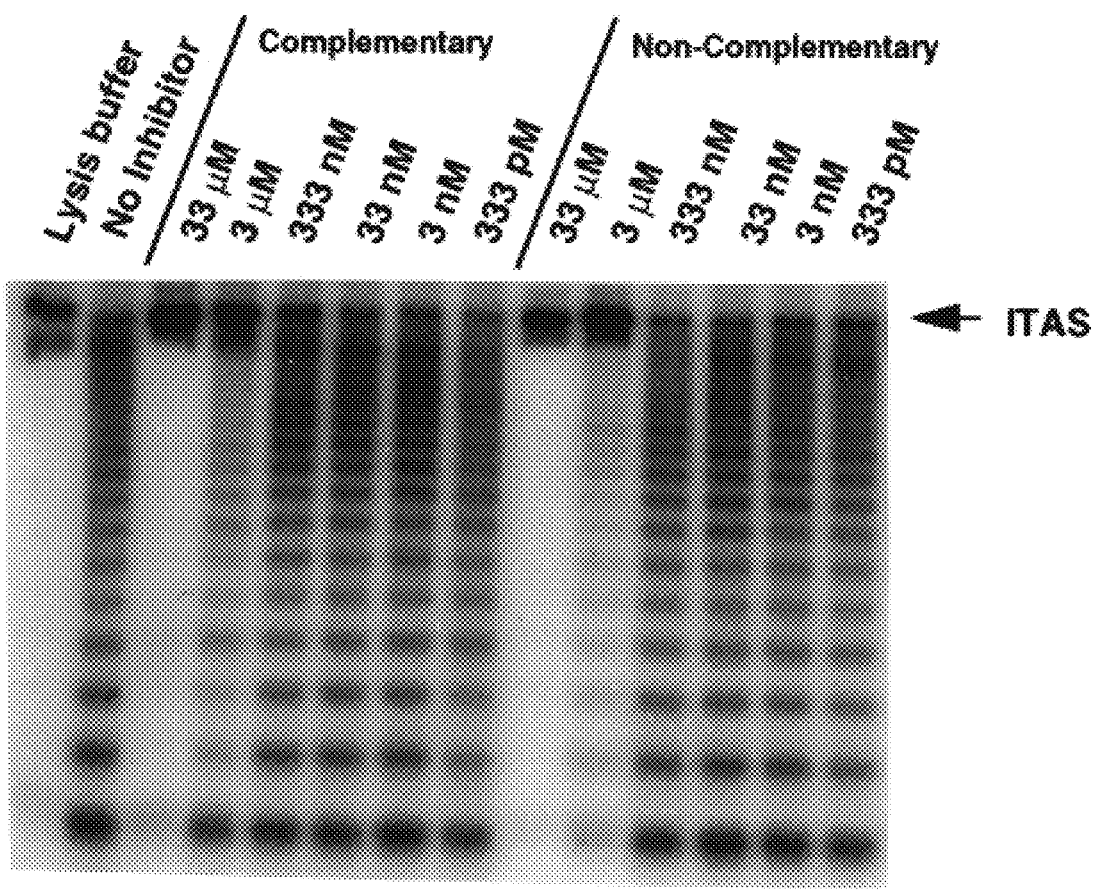
FIG. 6: Inhibition of telomerase activity by varied concentrations of complementary sequence PS oligonucleotide III, and inhibition of telomerase activity by varied concentrations of non-complementary sequence PS oligonucleotide V.

The relative efficiency of inhibition of telomerase activity by PNAs was put into context by comparison to inhibition by analogous phosphorothioate (PS) oligonucleotides. PS oligonucleotides were synthesized to be analogous in sequence to PNA XII, the most effective PNA inhibitor, and to other PNAs (Table 1). We observed that PS oligomers were inhibitors of telomerase activity (FIG. 6, panel A), although inhibition was not as potent as that for PNAS. For example, PS oligonucleotide III inhibited telomerase with an $IC_{50}$ of 50 nM, demonstrating a substantially lower inhibitory effect than that observed for its PNA homologue XII, which exhibited an $IC_{50}$ of 0.9 nM. Other PS oligomers that were also complementary to hTR were also inhibitors, although their ability to inhibit telomerase activity was less than that of their PNA homologues. However, by contrast to the high selectivity of inhibition by PNAs, which must possess complementarity to hTR to inhibit telomerase activity, PS oligonucleotides that had no complementarity to hTR also inhibited telomerase (FIG. 6, panel B). $IC_{50}$ values for the inhibition of telomerase activity by noncomplementary PS oligonucleotides were almost as potent as those observed for PS oligonucleotides that were complementary (Table 1). Neither PS oligonucleotide IV or V possess the ability to form G-quartet structures, indicating that formation of this motif is not necessary to block telomerase activity.

Most previous studies on the inhibition of protein function by oligonucleotides have utilized hybridization to mRNA to limit activity by preventing protein expression. Oligonucleotides, however, can also make specific hydrophobic, electrostatic, and Van der Waals contacts with proteins and thereby inhibit protein function directly. Ribonucleoproteins, macromolecules which consist of both RNA and protein, are a class of targets which can be inhibited by polymers capable of interacting with a polynucleotide component in a sequence-dependent manner.

The data disclosed herein demonstrates inhibition of the enzymatic activity of a ribonucleoprotein, telomerase, through hybridization of complementary oligonucleotides to its RNA component in a sequence-dependent manner. The sequence of the RNA template of human telomerase (hTR) has been determined (Feng et al. (1995) op.cit), affording the sequence information necessary to guide the design of additional oligomer-based inhibitors of the invention. The development of oligomer-based inhibitors of telomerase is especially attractive relative to other knowledge based approaches to inhibitor design, as neither the three dimensional structure of telomerase nor the primary sequence of its protein component are currently known in the art.

This example shows that PNAs, in spite of their inability to participate in backbone-based electrostatic interactions, bind to and effectively inhibit telomerase, and do so with $IC_{50}$ values as low as 0.9 nM. This efficient inhibition contrasts sharply with observations indicating that PNAs cannot inhibit SP6 or T7 RNA polymerase. RNA polymerases can only interact with nucleic acids through sequence selective binding between protein and inhibitory nucleic acid. The lack of an ability to form electrostatic interactions is not, however, an obstacle for inhibition of telomerase by PNAs, consistent with a model wherein WatsonCrick pairing of PNAs with hTR is sufficient for efficient inhibition.

The finding that PNAs complementary to hTR inhibit telomerase at concentrations as low as 0.3 nM and, conversely, that PNAs lacking sequence complementarity do not detectably inhibit, demonstrates that association of PNAs with telomerase can be stable, efficient, and selective. Such compounds might be utilized to probe the intracellular function of telomerase and might be adapted to test the hypothesis that the inhibition of telomerase leads to suppression of tumor growth. Aside from their demonstrated excellent inhibition of telomerase activity, PNAs are well suited as telomerase inhibitors because their high affinity for complementary nucleic acids makes it possible to adapt relatively short PNAs as effective inhibitors. This reduces the cost of inhibitor synthesis and possibly aid bioavailability and membrane permeability. PNA synthesis is based on standard t-boc (Thomson et al. (1995) *Tetrahedron* 51: 6179) or f-moc (Wittung et al. (1995) *op.cit*) based peptide chemistry, facilitating the synthesis of diverse PNA-peptide adducts or PNA-small molecule adducts. Such modifications yield PNA species that can have either increased membrane permeability, increased inhibition, or both. The high affinity of PNA association also indicates that PNAs can be employed as affinity ligands for purification of human telomerase and its associated proteins. The inability of PNAs to bind to proteins that interact with DNA via electrostatic interactions may also increase the specificity of telomerase isolation during purification.

By contrast to the high affinity and selectivity of the inhibition of telomerase activity by PNAS, inhibition by PS oligonucleotides is both less potent and less selective. Unlike the PNA backbone, PS linkages are negatively charged, resulting in electrostatic repulsion between the incoming PS oligonucleotides and the RNA target. PS bligonucleotides have lower melting temperatures for hybridization to complementary sequences than do the corresponding PNAs, and the less stable association probably contributes to the higher $IC_{50}$ values observed for inhibition of telomerase by PS oligonucleotides. Importantly, Watson-Crick pairing is not necessary for inhibition by PS oligonucleotides, as sequences that are not complementary to hTR inhibit telomerase activity with $IC_{50}$ values that are similar to those obtained through addition of complementary PS oligomers.

The observation that PS oligonucleotides inhibit telomerase activity non-selectively is consistent with a model wherein they possess a high affinity for either the protein component of telomerase or for non-template RNA and that this affinity does not depend on the nucleotide sequence of the PS oligomer. The finding that the TS primer possesses strong affinity for telomerase in spite of having only three bases complementary to hTR suggests that nucleic acids can take advantage of non-template interactions to increase binding, and the nonspecific binding of PS oligonucleotides may mimic these-interactions to generate stable association in the absence of base-pairing. T7 and SP6 RNA polymerase, reverse transcriptase, and other proteins also bind PS oligonucleotides nonsequence-specifically, indicating that non-selective binding is a general disadvantage of PS oligonucleotides.

The data indicates that PNAs inhibit the activity of human telomerase with high affinity and selectivity. Coupled with studies of the inhibition of SP6 and T7 RNAP by oligonucleotides it is clear that chemical modifications can substantially influence the ability of oligonucleotides to selectively inhibit enzyme activity. The selectivity of PNAs relative to PS oligonucleotides suggests that PNAs or other nonionic oligonucleotides may have important advantages for the recognition of complementary targets within complex cellular environments.

Example 2

PNA Scanning

1. Introduction

Targets for telomerase inhibition include the polymerase active site, the anchor site, RNA or protein domain interfaces, specialized structures that may be formed by newly synthesized telomeric DNA and the RNA template. Rational design of inhibitors aimed at the polymerase active site or at blocking domain assembly is complicated by the current lack of published data on amino acid sequence for any definitively identified mammalian telomerase protein component An oligonucleotide-based strategy that may generate highly selective inhibitors uses knowledge of the sequence of the RNA template (Feng et al., supra). Studies have demonstrated that addition of complementary DNA (Feng et al., supra) or peptide nucleic acid (PNA) (Norton et al., *Nature Biotech* 14: 615–619 (1996)) oligonucleotides can inhibit ciliate and mammalian telomerase activity.

PNA-mediated inhibition of human telomerase is sensitive to single nucleotide changes in register between short PNAs and overlapping target sequences within the RNA active site. Differences in inhibition caused by the addition or loss of the potential for single base pairs provides insights into the ability of active site nucleotides to contribute to recognition at a resolution that is now unobtainable through other methods.

2. Materials and Methods a. Oligomer Synthesis

Synthesis of peptide nucleic acids were carried out manually as described in Example 1. All PNAs were characterized by matrix assisted laser desorption time of flight (MALDI-TOF) mass spectrometry using a Voyager-DE mass spectrometry workstation (PerSeptive Biosystems). All PNAs contained glycine at the amino termini and lysine at the carboxy termini unless otherwise noted (Table 3). DNA oligonucleotides were synthesized on a Applied Biosystems (Foster City, Calif.) 451 DNA synthesizer.

b. Telomerase Assays

Telomerase activity was detected using the TRAPeze™ telomerase detection kit (Oncor, Gaithersburg, Md.) essentially as described) Holt, S. E., Shay, J. W. & Wright, W. E. (1996) *Nature Biotech* 14: 836–839). The source of telomerase was human immortal primary breast epithelial cell line (HME50-5). Cultured cells ($10^5$–$10^6$) were lysed as recommended in the protocol supplied by Oncor. Cell lysates containing 200 cell equivalents were preincubated at 25° C. for 30 minutes with PNA (0 to 100 $\mu$M, diluted in 10 mM Tris pH 8.3 and 10 $\mu$g ml$^{-1}$ bovine serum albumin (BSA)). PNAs sometime aggregated upon prolonged storage, so PNA stocks were briefly heated to 55° C. prior to addition to assay mixtures to ensure reproducible inhibition. Following preincubation, TRAPeze reaction mixture (20 mM Tris-HCl, pH 8.3, 1.5 mM $MgCl_2$, 63 mM KCl, 0.05% Tween 20, 1 mM EGTA, and 0.01% BSA, 50 $\mu$M dNTPs, and primer mix supplied in the kit) was added directly to the mixture of PNA and cell extract. This reaction was incubated at 25° C. for 30 minutes to allow telomerase to elongate the TS primer. For control experiments, PNAs were added to a final concentration of 3.3 $\mu$M immediately prior to amplification. The tubes were transferred to a PCR thermocycler, and a two-step cycle (30 sec 94° C. and 30 sec 60° C.) was performed 27 times. Samples were analyzed using nondenaturing polyacrylamide gel electrophoresis.

Telomerase products and an internal PCR control were quantitated by phosphorimager analysis (Molecular Dynamics). The lanes were divided into one region encompassing the telomerase products and another including the internal standard signal. The radioisotope density was integrated for each area, and the ratio of telomerase product to internal standard was determined. This value was normalized to a positive control (no PNA added) where the ratio of telomerase products to internal standard was assigned 100% activity. The extent inhibition was plotted against the final PNA concentration used in the preincubation reaction, and these graphs were used to estimate the $IC_{50}$ values.

c. Melting Temperature Determination

Melting temperature studies were performed spectrophotometrically by measuring the change in absorbance at 260 nm using a 8452A UV spectrophotometer (Hewlett Packard) and an HP 89090A Peltier temperature control accessory (TEMPCO Software). Determinations were done in a volume of 0.5 mL in a capped cuvette. Equimolar amounts of DNA and PNA (20 $\mu$M) were denatured at 90° C. for 5 min in 1.0 M $KH_2PO_4/K_2HPO_4$ pH 7.6 and reannealed upon cooling to room temperature over 20 minutes. Absorbance was recorded from 25° C. to 90° C. in 4° C. or 5° C. increments using a 2 minute equilibration time between each measurement. DNA oligonucleotides used for measuring $T_m$ values, and their complementary PNAs were as follows; 5'-TTTGTCTAACCCTAACTGAGAAGG-3' (SEQ ID NO:25) (PNA 4–9, 23, and 24; 5' CCATTTTTGTCTAACCCTAACT-3' (SEQ ID NO:26) (PNAs 1–3); 5'-TAACTGAGAAGGGCGT-3' (SEQ ID NO:27) (PNAs 13–16); 5'-ACCCTAACTGAGAAG-3' (SEQ ID NO:28) (PNAs 10–11); 5'-ACCCTAACTG-3' (SEQ ID NO:29) (PNAs 20–21); 5'-ACCCTAAC-3' (SEQ ID NO:30) (PNAs 18, 19, 25–28); 5'-CTAACCCTAAC-3' (SEQ ID NO:31) (PNAs 7 and 17); 5'-CTAACTCTAAC-3' (SEQ ID NO:32) (PNAs 7, 17).

3. Results a. Inhibition of Telomerase by PNAs

A series of PNAs were designed to progressively overlap the telomerase RNA template. These PNAs were incubated with telomerase-containing cell extracts derived from a human immortal primary breast epithelial cell line (HME50-5) and assayed their influence on telomerase activity using the telomere repeat amplification protocol (TRAP) (Holt et al., supra). In this protocol, telomerase extends an oligonucleotide primer to form elongation products. These products are then amplified by PCR to facilitate their detection. TRAP affords a sensitive and linear response over. the range of telomerase activity used in these studies (Holt et al., supra) and inclusion of an internal amplification standard in each sample permits reproducible quantitation. Appearance of the internal amplification standard also ensures that added PNAs are not interfering with Taq polymerase during amplification.

As a further control, PNAs were introduced at concentrations at least 10 times greater than the measured $IC_{50}$ value directly before initiating PCR and monitored the effect of this addition on the amplification of telomerase products. This control was necessary to ensure that PNAs were not inhibiting the appearance of elongation products by interfering with primer or template during PCR. These additions did not reduce the appearance of amplified telomerase products, confirming that the inhibition described below is due to sequence-selective PNA-mediated inhibition of telomerase activity.

b. Effect of Recognition of Cytidines 50–52 by Overlapping PNAs

The analysis began with PNA 1, which was complementary to the last three nucleotides at the 5' end of the RNA template and adjacent non template nucleotides. PNA 1 did not effectively inhibit telomerase activity (Table 2), a result that is consistent with observations from reconstitution experiments by Greider and coworkers showing that the region adjacent to the 5' terminus of the template region of human telomerase is not essential for telomerase activity. PNAs 2, 3, and 4 progressively overlap three cytidines (C50–C52) within the center of the RNA active site. Recognition of one of these cytidines (C50) by PNA 2 did not result in significant inhibition, while recognition of C50–51 by PNAs 3 or C50–52 by PNA 4 led to $IC_{50}$ values of 100 nM and 10 nM respectively (Table 2).

Scanning toward the 3' end of the template yielded PNAs 5–9 that inhibited telomerase with $IC_{50}$ values of 1–10 nM. Increased inhibition by PNA 5 relative to PNA 4 indicates that nucleotides U53 and A54 participate in PNA recognition, although this effect is not as dramatic as that observed with C51 and C52. Scanning PNAs 10–12 began to progressively expose C50–52 from the 5' direction and resulted in an increase in $IC_{50}$ values from 10 to 300 nM, a result that supports C50–52 as a critical determinant for PNA-mediated inhibition. To further examine the importance of C50–52, PNA 17 was assayed containing a mismatched adenine opposite the central cytidine (C51). This alteration reduced inhibition by 1000-fold, emphasizing the exquisite sensitivity of PNA recognition to exact complementarity at the target site, a result consistent with those observed by Nielsen and coworkers for hybridization to DNA or RNA oligonucleotides. Addition of adjacent PNAs in tandem (PNAs 11 and 3, Table 2) did not result in improved inhibition, suggesting that binding at the domain interface is not cooperative.

These results demonstrate that C50–52 are accessible for PNA recognition and are important determinants for PNA-meditated inhibition of human telomerase activity. It is interesting to note that C50–52 are at the junction of the 3' telomerase RNA domain that binds to telomere ends and the 5' domain that acts as template for strand elongation). The importance of recognition of these nucleotides for inhibition may reflect the requirement for them to be accessible during these critical events. The importance of C50–52 also suggests that they can be the target for the design of a novel class of small molecule inhibitors that can combine binding to cytidine triplets with recognition of additional telomerase-specific determinants.

c. Effect of Recognition of the 3' Region of the RNA Template by PNAs

Scanning was extended back toward the 3' end of the telomerase RNA by synthesizing PNAs 12–15. These PNAs continued to inhibit telomerase with $IC_{50}$ values of approximately 300–500 nM. Between six and nine nucleotides of these PNAs are complementary to RNA past the 3' termini of the active site (C56 to G63), and inhibition suggests that some of these nucleotides must be accessible for hybridization. This conclusion is supported by earlier observations that the analogous 3' region within the Tetrahymena RNA component is accessible to in vivo methylation footprinting. As PNA's 15 and 16 reached the extreme 3' end of the alignment domain $IC_{50}$ values increased to 0.5 µM and 10 µM respectively. The jump in $IC_{50}$ from 0.5 µM to 10 µM upon losing the ability to recognize C56 indicates that this cytidine is accessible and important for oligomer recognition. Accessibility of C56 is consistent with the assumption that it is available to recognize and align substrate DNA. The lack of strong inhibition by PNAs 16 reflects the fact that nucleotides needed to recognize DNA substrates are no longer covered by the PNA, and suggests that the RNA sequence to the 3' side can be blocked without significantly affecting chain elongation.

d. Measurement of Melting Temperatures of PNAs to Complementary Sequences

Melting temperatures were measured ($T_m$) of duplexes between PNAs and their DNA complements to ensure that the PNAs used in these studies could form duplexes with complementary sequences at the assay temperature of 25° C. DNA oligonucleotides were used because employment of DNA rather than RNA facilitated analysis of the large number of PNAs that required assay. Comparison to RNA:PNA melting temperatures is justified because $T_m$'s for PNA:DNA and PNA:RNA hybrids are similar. PNAs 2, 3 and 4 that varied 3000-fold in $IC_{50}$ values had similar melting temperatures of 63, 66, and 67° C. respectively (Table 2), demonstrating that their differing potentials for binding complementary sequences were not responsible for the large differences in inhibition. Similarly, PNAs 10–16 which inhibit less all have melting temperatures that significantly exceed the assay temperature (Table 3). The level of inhibition of telomerase is at least partially governed by structural and functional determinants that are unique to telomerase and do not simply reflect the affinity of complementary pairing as measured by the melting temperature of isolated single strands.

Interestingly, PNAs containing three consecutive guanines exhibit substantially higher melting temperatures than similar PNAs that contain three cytidines (Table 2). For example, the eleven nucleotide PNA 15 of sequence GCCCTTCTCAG (SEQ ID NO:33) possessed a $T_m$ of 56° C., while the eleve nucleotide PNA 4 of sequence GGGT-TAGACAA (SEQ ID NO:11) exhibited a $T_m$ of 67° C., despite the fact that the ratio of guanine to cytidine within PNA 4 is lower than that of PNA 15. PNA 17, in which recognition of consecutive cytidines is disrupted by insertion of adenine in place the central guanine exhibits a reduction of $T_m$ relative to PNA 7 from 65° C. to 53° for hybridization to an exactly complementary DNA oligonucleotide containing, and 39° C. to a mismatched complement (Table 2). These results suggests that consecutive guanines within a PNA permit tight binding to target sequences relative to analogous PNAs containing consecutive cytidines, a phenomenon that may contribute to the importance of recognition of C50–52 for optimal inhibition of human telomerase by PNAs.

e. Use of Critical Binding Determinants to Identify Minimal PNA Inhibitors

Earlier studies (see Example 1) of PNA-mediated inhibition of telomerase demonstrated efficient inhibition by PNAs 11–13 ucleotides in length, with 1000–10,000 fold lower inhibition by shorter PNAs. However, none of the shorter PNAs assayed in the previous study had been designed to recognize both the critical determinants for inhibition identified by our PNA scanning—the 3' end of the template, C56, and the internal cytidine triad, C50–52. This information was used to synthesize a series of PNAs six to ten nucleotides in length, that were anchored at A49, directly adjacent to the 5' side of the cytidine triad, and moved progressively toward the 3' end of the template. In all cases the measured melting temperatures (35–59° C.) were substantially above the assay temperature of 25° C. (Table 3). PNAs 18 and 19 containing six or seven nucleotides were poor inhibitors, while PNAs 20–22 containing eight, nine or ten nucleotides inhibited with $IC_{50}$ values of 300, 40, and 10 nM respectively (Table 3). The additional inhibition observed upon recognition of C56 and U57 demonstrates that these nucleotides are available for recognition. Recognition of C50–52, while necessary, is not sufficient for optimal inhibition by PNAs, and that inhibition can be increased by also recognizing C56 and U57. The value of identification of accessible determinants for inhibitor design is emphasized by the finding that eight nucleotide PNA 20 ($T_m$=47° C.) that recognizes both C50–52 and C56 inhibits better than nine nucleotide PNA 23 ($T_m$=58° C.) that recognizes C50–52 but not C56 (Table 2).

f. Effect of N-terminal Modification on PNA Inhibition

Further enhanced inhibition was attempted by synthesizing PNAs 25–27 containing chemically modified N-termini. The hypothesis was that these modifications might form hydrophobic interactions with either the RNA or the protein component that would act to stabilize PNA binding. While acylated and acridine-modified PNAs did possess significantly higher melting temperatures to complementary DNA oligomers (Table 3) than did unmodified PNA 24, inhibition of human telomerase was not significantly enhanced. Apparently these chemical modifications either cannot make the contacts responsible for increasing hybridization to an isolated complementary oligonucleotide, or they can make contacts but these are not relevant for enhancing inhibition. While these experiments are inconclusive regarding the potential for terminal modifications to enhance inhibition of telomerase activity, the fact that PNAs can be readily modified suggests that as human telomerase becomes available in larger quantities PNAs may be a valuable tool for delivery of affinity labels to map reactive amino acids and nucleotides near the RNA active site.

g. Optimization of Inhibition by Taking Advantage of Known Determinants C50–52, C56, and U57

Both PNA length and position relative to the RNA active site are critical for optimal inhibition. Once it was established that C50–52, C56, and U57 were determinants for PNA-mediated inhibition an eight nucleotide PNA was synthesized to span the region they define. This PNA exhibited an $IC_{50}$ value of 30 nM, the lowest for any eight nucleotide PNA assayed and 30-fold lower than 9-nucleotide PNA 23 that only recognized C50–52. This potent inhibition is achieved in spite of PNA 28 possessing a melting temperature of 47° C., eleven degrees lower than that of PNA 23. This result demonstrates that PNA inhibition can be progressively refined as determinants of recognition are identified.

h. Importance of Other Nucleotides Within the RNA Active Site

PNA scanning confirms the accessibility of nucleotides C50–52, C56, and U57 for base-pairing. Why should recognition of some nucleotides be especially critical for PNA-mediated recognition? The RNA active site must function in conjunction with the protein subunits, and may be involved in structural interactions with these subunits or with other regions of the RNA. As a result, all eleven nucleotides may not be equally available for optimal base-pairing with inhibitory oligomers when the ribonucleoprotein is not bound to substrate. Furthermore, once bound, some PNAs may be more susceptible than others to displacement during polymerization. These results do not exclude the possibility that other nucleotides play important roles in oligomer recognition, and scanning strategies using shorter PNAs or PNAs containing systematically placed mismatches can be used to identify more subtle contributions to inhibitor recognition. Results gained from probing with PNAs should complement those gained from mutagenesis and mapping using nucleases or metal-dependent cleavage to afford a more definitive picture of RNA accessibility, structure, and function.

i. Conclusion

These studies introduce PNA scanning as an approach for systematically mapping the recognition of complex nucleic acids. Series of PNAs can be readily synthesized, and this method should be widely applicable. The importance of recognition of RNA nucleotides within the RNA active site of human telomerase to inhibitors differs and that cytidines 50–52, 56, and uridine 57 are important determinant; for inhibition of telomerase. At a minimum, these results indicate that these nucleotides are physically exposed for inhibitor binding. Cytidines 50–52 occur at the functional boundary between the alignment and elongation domains, and may represent a physical boundary element as well. The accessible nucleotides identified facilitated the design of small PNA inhibitors and they can be key recognition elements for inhibition of human telomerase by even smaller molecules.

TABLE 2

Effect on the inhibition of telomerase activity of the position of PNA relative to the eleven nucleotide telomerase RNA active site.

|  | Sequence | $IC_{50}$ ($\mu$M) | $T_m$ ° C. | SEQ ID NO: |
|---|---|---|---|---|
|  | 3'GAUGCGGGAAGAGUCAAUCCCAAUCUGUUUU5' |  |  | 49 |
| 1 | NH2-TAGACCAAAAAATG-COOH | >30 | 63 | 50 |
| 2 | GTTAGACAAAAAA | >30 | 63 | 51 |
| 3 | GGTTAGACAAAAA | 0.10 | 66 | 52 |
| 4 | GGGTTAGACAA | 0.01 | 71 | 3 |
| 5 | TAGGGTTAGACAA | 0.001 | 75 | 4 |
| 6 | GTTAGGGTTAGAC | 0.01 | 73 | 12 |
| 7 | GTTAGGGTTAG | 0.01 | 64 | 13 |
| 8 | CAGTTAGGGTTAG | 0.001 | 72 | 1 |
| 9 | CTCAGTTAGGG | 0.01 | 65 | 14 |
| 10 | TCTCAGTTAGG | 0.3 | 58 | 53 |
| 11 | TTCTCAGTTAG | 0.3 | 52 | 54 |
| 12 | CCCTTCTCAGTTA | 0.3 | 57 | 55 |
| 13 | CGCCCTTCTCAGT | 0.3 | 58 | 56 |
| 14 | CCCTTCTCAGT | 0.4 | 48 | 57 |
| 15 | GCCCTTCTCAG | 0.5 | 56 | 33 |
| 16 | CGCCCTTCTCA | 10 | 53 | 58 |
| 17 | GTTAGaGTTAG | >30 | 33 (. mismatch) | 59 |

TABLE 2-continued

Effect on the inhibition of telomerase activity of the position of PNA relative to the eleven nucleotide telomerase RNA active site.

| | Sequence | IC$_{50}$ (μM) | T$_m$ °C. | SEQ ID NO: |
|---|---|---|---|---|
| 11/3 | TTCTCAGTTAG/GGTTAGACAAAAAA | 0.1 | 56 (w. complement) | 54/52 |

The RNA active site and complementary nucleotides within PNAs are underlined and in boldface. Numbering of telomerase RNA is noted (Feng et al., 1994). PNA 17 contains an adenine (lower case) that would be mismatched opposite C51.

TABLE 3

Effect on PNA size and terminal modification on inhibition of telomerase activity and melting temperature

| | Sequence | IC$_{50}$ (μM) | TM° C. | SEQ ID NO: |
|---|---|---|---|---|
| | 3'-AAGAGUCAAUCCCAAUCUG-5' | | | 60 |
| 18 | NH$_2$Gly-TAGGGT-COOH | 30 | 35 | — |
| 19 | Gly-TTAGGGT | 20 | 39 | — |
| 20 | Gly-GTTAGGGT | 0.3 | 47 | — |
| 21 | Gly-AGTTAGGGT | 0.04 | 54 | — |
| 22 | Gly-CAGTTAGGGT | 0.01 | 59 | — |
| 23 | Gly-TAGGGTTA | 1 | 58 | — |
| 24 | GTTAGGGT | 0.2 | 52 | — |
| 25 | Ac-GTTAGGGT | 0.3 | 54 | — |
| 26 | Bz-GTTAGGGT | 0.2 | 50 | — |

TABLE 3-continued

Effect on PNA size and terminal modification on inhibition of telomerase activity and melting temperature

| | Sequence | IC$_{50}$ (μM) | TM° C. | SEQ ID NO: |
|---|---|---|---|---|
| 27 | Acr-GTTAGGGT | 0.3 | 60 | — |
| 28 | AGTTAGGG | 0.03 | 47 | — |

Underlined and boldfaced nucleotides are those identified during initial PNA scanning (Table 2) as being critical for optimal inhibition. All PNAs contained a C-terminal lysine. N-terminal modifications, if any, are noted. Ac, acyl; Bz, benzyl; Acr, acridine.

The foregoing examples describe various aspects of the invention and how certain compounds of the invention were made. The examples are not intended to provide an exhaustive description of the many different embodiments of the invention encompassed by the following claims.

All publications and patent applications cited in this specification are herein incorporated by reference as if each individual publication or patent application were specifically and individually indicated to be incorporated by reference.

What is claimed is:

1. A peptide nucleic acid ("PNA") comprising a sequence of six to twenty-five nucleobases, wherein said sequence comprises a nucleobase sequence GTTAGGG, wherein said peptide nucleic acid hybridizes to the RNA component of mammalian telomerase.

2. The PNA of claim 1, wherein said sequence comprises AGTTAGGG.

3. The PNA of claim 1, comprising no more than twenty-five nucleobases.

4. The PNA of claim 1, further comprising
at least one amino-terminal amino acid; and
at least one carboxy-terminal amino acid.

5. The PNA of claim 1, further comprising from 1 to 10,000 covalently linked nucleotides.

6. The PNA of claim 1, further comprising from 1 to 10,000 covalently linked amino acids.

7. The PNA of claim 1, wherein said sequence is selected from the group consisting of: CAGTTAGGGTTAG (SEQ ID NO:1); CTCAGTTAGGGTTAG (SEQ ID NO:2); GTTAGGGTTAGACAA (SEQ ID NO:5); AGTTAGGGTTAG (SEQ ID NO:8); CCCTCTCAGTTAGGGTT (SEQ ID NO:9); GTTAGGGTTAGAC (SEQ ID NO:12); GTTAGGGTTAG (SEQ ID NO:13); CTCAGTTAGGG (SEQ ID NO:14); GTTAGGGT (SEQ ID NO:15); AGTTAGGGT (SEQ ID NO:16); and CAGTTAGGGT (SEQ ID NO:17).

8. The PNA of claim 1 selected from the group consisting of: CAGTTAGGGTTAG (SEQ ID NO:1); CTCAGTTAGGGTTAG (SEQ ID NO:2); GTTAGGGTTAGACAA (SEQ ID NO:5); AGTTAGGGTTAG (SEQ ID NO:8); CCCTCTCAGTTAGGGTT (SEQ ID NO:9); GTTAGGGTTAGAC (SEQ ID NO:12); GTTAGGGTTAG (SEQ ID NO:13); CTCAGTTAGGG (SEQ ID NO:14); GTTAGGGT (SEQ ID NO:15); AGTTAGGGT (SEQ ID NO:16); and CAGTTAGGGT (SEQ ID NO:17).

9. The PNA of claim 6, wherein said covalently linked amino acids comprise a polypeptide sequence that enhances cellular uptake of said peptide nucleic acid, wherein said polypeptide sequence is selected from the group consisting of the h-region of a signal peptide and the 3rd helix of Antp-HD.

10. The PNA of claim 9 selected from the group consisting of:

NH2-GlyGlyArgGlnIleLysIleTrpPheGlnAsnArgArgMet-LysTrpLysLys-GTTAGGGTTAG (SEQ ID NO:18); and NH2-GTTAGGGTTAG-GlyGlyArgGlnIleLys-IleTrpPheGlnAsnArgArgMetLysTrpLysLys-COOH (SEQ ID NO:19).

11. A composition comprising said PNA of claim 1 and an excipient or delivery vehicle.

12. The composition of claim 11, wherein said delivery vehicle is a liposome formulation.

13. The composition of claim 12, wherein said PNA is selected from the group consisting of: CAGTTAGGGTTAG (SEQ ID NO:1); CTCAGTTAGGGTTAG (SEQ ID NO:2); GTTAGGGTTAGACAA (SEQ ID NO:5); AGTTAGGGTTAG (SEQ ID NO:8); CCCTCTCAGTTAGGGTT (SEQ ID NO:9); GTTAGGGTTAGAC (SEQ ID NO:12); GTTAGGGTTAG (SEQ ID NO:13); CTCAGTTAGGG (SEQ ID NO:14); GTTAGGGT (SEQ ID NO:15); AGTTAGGGT (SEQ ID NO:16); and CAGTTAGGGT (SEQ ID NO:17).

* * * * *